(12) United States Patent
Elizondo, II

(10) Patent No.: US 10,185,854 B2
(45) Date of Patent: *Jan. 22, 2019

(54) MEDICAL ARTICLE TRACKING USING HYBRID ISOLATED MAGNETIC DIPOLE PROBE WITH ENERGY PATTERN CONTROL

(71) Applicant: MEPS Real-Time, Inc., Carlsbad, CA (US)

(72) Inventor: Paul M. Elizondo, II, Escondido, CA (US)

(73) Assignee: MEPS Real-Time, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/785,389

(22) Filed: Oct. 16, 2017

(65) Prior Publication Data

US 2018/0039803 A1    Feb. 8, 2018

Related U.S. Application Data

(63) Continuation of application No. 14/752,837, filed on Jun. 27, 2015, now Pat. No. 9,792,476.

(51) Int. Cl.
*A61J 7/00* (2006.01)
*G06K 7/00* (2006.01)
(Continued)

(52) U.S. Cl.
CPC ........ *G06K 7/10366* (2013.01); *A61J 7/0084* (2013.01); *G06F 19/00* (2013.01);
(Continued)

(58) Field of Classification Search
CPC ............ G08B 13/14; H01Q 9/00; G06F 19/00
USPC ............. 340/572.1–572.9, 10.1–10.5, 568.1; 343/747, 702, 895; 361/113, 56, 91, 111; 235/383, 385
See application file for complete search history.

(56) References Cited

U.S. PATENT DOCUMENTS 2,457,919 A    1/1949 Ramsey
3,478,818 A    11/1969 Tetsuya Kohya et al.
(Continued)

OTHER PUBLICATIONS

PCT International Search Report for International Application No. PCT/US2016/039090 dated Oct. 5, 2016, 3 pages.

*Primary Examiner* — Nam V Nguyen
(74) *Attorney, Agent, or Firm* — Thomas A. Runk; Brooks Kushman P.C.

(57) ABSTRACT

A system and method for tracking medical articles located in a container includes a hybrid isolated magnetic dipole ("IMD") probe that provides an activating EM energy RF field having a magnetic near field at least as great as the electric near field, both of which cover the entire interior of the container. The probe comprises a main element having capacitive coupling across at least one slot and spacing above a ground plane to thereby form an isolated electric field and an equally strong or stronger magnetic field that fills the interior of the container to activate RFID tags therein. A dual system is provided for larger containers. A dynamic impedance tuning system controls the probe impedance for increased efficiency in transferring power to the interior of the container. Beam steering is provided with the IMD probe.

26 Claims, 10 Drawing Sheets

(51) Int. Cl.
  *G06K 7/10* (2006.01)
  *G07G 1/00* (2006.01)
  *H01Q 1/24* (2006.01)
  *H01Q 9/00* (2006.01)
  *H01Q 9/28* (2006.01)
  *G06F 19/00* (2018.01)
  *G06Q 10/08* (2012.01)
  *G07F 17/00* (2006.01)
  *G08B 13/14* (2006.01)
  *G16H 40/20* (2018.01)

(52) U.S. Cl.
  CPC ....... *G06F 19/3462* (2013.01); *G06K 7/0008* (2013.01); *G06K 7/10158* (2013.01); *G06Q 10/087* (2013.01); *G07F 17/0092* (2013.01); *G07G 1/009* (2013.01); *G08B 13/14* (2013.01); *G16H 40/20* (2018.01); *H01Q 1/24* (2013.01); *H01Q 9/00* (2013.01); *H01Q 9/28* (2013.01); *A61J 2205/60* (2013.01)

(56) References Cited

U.S. PATENT DOCUMENTS

| | | | |
|---|---|---|---|
| 6,058,000 A | | 5/2000 | Koenck et al. |
| 6,703,935 B1 | * | 3/2004 | Chung ............... G06K 7/10316 340/572.1 |
| 6,906,667 B1 | | 6/2005 | Poilasne et al. |
| 6,943,730 B2 | | 9/2005 | Poilasne et al. |
| 7,154,449 B2 | | 12/2006 | Liu et al. |
| 7,310,070 B1 | | 12/2007 | Hardman et al. |
| 7,448,544 B1 | * | 11/2008 | Louie ................. G06F 19/3462 235/385 |
| 7,518,516 B2 | | 4/2009 | Azevedo et al. |
| 7,753,272 B2 | | 7/2010 | Harper et al. |
| 7,777,686 B2 | | 8/2010 | Desclos et al. |
| 7,830,320 B2 | | 11/2010 | Shamblin et al. |
| 7,884,725 B2 | | 2/2011 | Kruest et al. |
| 7,911,402 B2 | | 3/2011 | Rowson et al. |
| 8,174,392 B1 | * | 5/2012 | Saghbini ............ G06F 19/3462 340/572.8 |
| 8,421,702 B2 | | 4/2013 | Desclos et al. |
| 8,749,356 B2 | | 6/2014 | Hussain et al. |
| 8,907,531 B2 | | 12/2014 | Hall et al. |
| 9,013,307 B2 | | 4/2015 | Hussain et al. |
| 9,792,476 B2 | * | 10/2017 | Elizondo, II ....... G06K 7/10366 |
| 2007/0268133 A1 | | 11/2007 | Sanchez et al. |
| 2008/0004908 A1 | | 1/2008 | Oh et al. |
| 2008/0094214 A1 | | 4/2008 | Azevedo et al. |
| 2009/0001093 A1 | | 1/2009 | Labhard |
| 2010/0126052 A1 | | 5/2010 | Rice |
| 2013/0085766 A1 | | 4/2013 | Bojarski et al. |
| 2013/0111936 A1 | | 5/2013 | Olson |
| 2015/0161558 A1 | | 6/2015 | Gitchell et al. |

* cited by examiner

MEDICAL ARTICLE TRACKING USING HYBRID ISOLATED MAGNETIC DIPOLE PROBE WITH ENERGY PATTERN CONTROL

This application is a continuation of U.S. application Ser. No. 14/752,837, filed Jun. 27, 2015, now U.S. Pat. No. 9,792,476, which applicant incorporates by reference.

The invention generally relates to a system and method for providing energy to a container to activate devices in the containers to respond with identification data, and more particularly, to a system and method that provides energy having magnetic field dominance in the near field of the activation energy to activate wireless devices, and that also includes directional energy control.

BACKGROUND

Medications and other medical articles designated for certain patients, whether prescription or over-the-counter, are often stored in cabinets that may or may not be refrigerated. Accurate inventory tracking of medical articles is imperative to be sure that the needed medical articles are where they should be, that there are enough of them, and when used, that they are accounted for. Other reasons for tracking medical articles include monitoring expiration dates, recalls, and various other factors. Detection of supply depletion is also a purpose of tracking medical articles. Such cabinets may consist of refrigerators ranging in size from quite small to quite large, to non-refrigerated cabinets, to cabinets having a plurality of stacked drawers, to single trays each of which has a predetermined collection of medical articles. Containers may be locked or unlocked. Locked containers may include electrically-controlled mechanical locks that are opened by matching the identification of a user with authorized users contained in a database. Other containers for storing or transporting medical articles are encountered in a healthcare environment.

In another system becoming more in demand, medical articles are tracked from the manufacturer's facility to delivery at the healthcare facility, and all through the healthcare facility until the medical articles are either administered to a patient or disposed of in some other way.

An important use of such wireless tracking systems is to be sure that the correct patient receives the correct medication. Positively identifying the patient with an identification device, positively identifying a medication with a wireless tracking device, and using a database that ties the two together can be a highly effective system in avoiding medication errors.

Among the current systems being used for the tracking of items, the barcode tracking system is wireless and has advantages. Wireless barcode tracking systems continue to present a useful alternative, especially in retail stores and other areas where use of a line of sight reader does not present a problem. However in the healthcare field where medical cabinets are used, a line of sight system is less preferable. Some cabinets store many medical articles and reading each one by scanning it with a barcode reader can involve too much time for busy healthcare personnel. Instead, a wireless system that does not require a line of sight tracking system to identify medical articles would be preferable.

In the healthcare field, a radio frequency identification ("RFID") tracking system has been found to excel. The RFID system does not require line of sight to make the identification. RFID systems typically include RFID stickers or labels, i.e., a sticker or label that includes an RFID tag, affixed to the inventory item, e.g., bottles, vials, boxes, syringes, bandages, etc. In a predominant system available today, each RFID tag has a unique identification number.

Each medical article has an RFID tag attached and the identification number of the RFID tag is entered into a database and correlated with the name of the medical article to which the tag is attached. A processor programmed to read the database matches that RFID tag identification number to the medical article to which it was originally attached so that the particular medical article can be determined to be present in the container. The database often includes an array of the data regarding the medical article to which the RFID tag is attached, such as the name, dose, manufacture date, expiration date, temperature requirements, and other data.

In another embodiment, the RFID tag itself has a programmable memory that can be programmed with identifying data about the nature of the very medical article to which it is attached thereby immediately identifying the medical article without the need to refer to a database. EPC Gen2/ISO 18000-63 standard RFID tags are available in many different configurations. Some of these tags are delivered preprogrammed with a 48-bit read-only write-protected unique ID. These preprogrammed tags with a unique ID are the same price as those tags that do not have a preprogrammed unique ID. This system also has advantages.

RFID tags may be incorporated into or attached to articles to be tracked. In some cases, the tag may be attached to the outside of an article with adhesive, tape, or other means and in other cases, the tag may be inserted within the article, such as being included in the packaging, located within the container of the article, or sewn into a garment. Some RFID tags are manufactured with a unique identification number which is typically a simple serial number of a few bytes with a check digit. In some cases, no check digit is stored. the error correction codes are generated on the fly by the RFID tag and reader. This identification number is incorporated into the tag during manufacture. The user cannot alter this serial/identification number and manufacturers guarantee that each serial number is used only once. This configuration represents the low cost end of the technology in that the RFID tag is read-only and it responds to an interrogation signal only with its identification number. Typically, the tag continuously responds with its identification number. Data transmission to the tag is not possible. These tags are very low cost and are produced in enormous quantities. There are no EPC Gen2/ISO 18000-63 standard based RFID tags currently available in the configuration described above. The simplest RFID tags conforming to these standards include a minimum of 96 bits of programmable memory.

Such read-only RFID tags typically are permanently attached to an article to be tracked and, once attached, the serial number of the tag is associated with its host article in a computer database. For example, a particular type of medicine may be contained in hundreds or thousands of small vials. Upon manufacture, or receipt of the vials at a health care institution, an RFID tag is attached to each vial. Each vial with its permanently attached RFID tag will be checked into the database of the health care institution upon receipt. The RFID identification number may be associated in the database with the type of medicine, size of the dose in the vial, and perhaps other information such as the expiration date of the medicine. Thereafter, when the RFID tag of a vial is interrogated and its identification number read, the database of the health care institution can match that identification number with its stored data about the vial. The contents of the vial can then be determined as well as any other characteristics that have been stored in the database. This system requires that the institution maintain a comprehensive database regarding the articles in inventory rather than incorporating such data into an RFID tag.

An object of the tag is to associate it with an article throughout the article's life in a particular facility, such as a manufacturing facility, a transport vehicle, a health care facility, a storage area, or other, so that the article may be located, identified, and tracked, as it is moved. For example, knowing where certain medical articles reside at all times in a health care facility can greatly facilitate locating needed medical supplies when emergencies arise. Similarly, tracking the articles through the facility can assist in generating more efficient dispensing and inventory control systems as well as improving work flow in a facility. Additionally, expiration dates can be monitored and those articles that are older and about to expire can be moved to the front of the line for immediate dispensing. This results in better inventory control and lowered costs.

RFID tags may be applied to containers or articles to be tracked by the manufacturer, the receiving party, or others. In some cases where a manufacturer applies the tags to the product, the manufacturer will also supply a respective database file that links the identification number of each of the tags to the contents of each respective article. That manufacturer supplied database can be distributed to the customer in the form of a file that may easily be imported into the customer's overall database thereby saving the customer from the expense of creating the database.

Many RFID tags used today are passive in that they do not have a battery or other autonomous power supply and instead, must rely on the interrogating energy provided by an RFID reader to provide power to activate the tag. Passive RFID tags require an electromagnetic field of energy of a certain frequency range and certain minimum intensity in order to achieve activation of the tag and transmission of its stored data. RFID tags may be activated by electric field energy and by magnetic field energy. Another choice is an active RFID tag; however, such tags require an accompanying battery to provide power to activate the tag, thus increasing the expense of the tag and making them undesirable for use in a large number of applications.

Depending on the requirements of the RFID tag application, such as the physical size of the articles to be identified, their location, and the ability to reach them easily, tags may need to be read from a short distance or a long distance by an RFID reader. Such distances may vary from a few centimeters to ten or more meters. Additionally, in the U.S. and in other countries, the frequency range within which such tags are permitted to operate is limited. As an example, lower frequency bands, such as 125 KHz and 13.56 MHz, may be used for RFID tags in some applications. At this frequency range, the electromagnetic energy ("EM") is less affected by liquids and other dielectric materials, but suffers from the limitation of a short interrogating distance. At higher frequency bands where RFID use is permitted, such as 915 MHz and 2.4 GHz, the RFID tags can be interrogated at longer distances, but they de-tune more rapidly as the material to which the tag is attached varies. It has also been found that at these higher frequencies, closely spaced RFID tags will de-tune each other as the spacing between tags is decreased.

Providing an internal RFID system in such a cabinet can pose challenges. Where internal articles can have random placement within the cabinet, the RFID system must be such that there are no "dead zones" that the RFID system is unable to reach. In general, dead zones are areas in which the level of coupling between an RFID reader antenna and an RFID tag is not adequate for the system to perform a successful read of the tag. The existence of such dead zones may be caused by orientations in which the tag and the reader antennae are in orthogonal planes. Thus, articles placed in dead zones may not be detected thereby resulting in inaccurate tracking of tagged articles. Fresnel zones (null energy and high energy regions) occur when reflected RF energy collides with transmitted energy or other reflected energy waves. The most common null energy region (dead zone) occurs when reflected energy collides with transmitted energy at ninety degrees out of phase.

Often in the medical field, there is a need to read a large number of tags attached to articles in such an enclosure, and as mentioned above, such enclosures have limited access due to security reasons. The physical dimension of the enclosure may need to vary to accommodate a large number of articles or articles of different sizes and shapes. In order to obtain an accurate identification and count of such closely-located medical articles or devices, a robust electromagnetic energy field must be provided at the appropriate frequency within the enclosure to surround all such stored articles and devices to be sure that their tags are all are activated and read. Such medical devices may have the RFID tags attached to the outside of their containers and may be stored in various orientations with the RFID tag (and associated antenna) pointed upwards, sideways, downward, or at some other angle in a random pattern.

Generating such a robust EM energy field is not an easy task. Where the enclosure has a size that is resonant at the frequency of operation, it can be easier to generate a robust EM field since a resonant standing wave may be generated within the enclosure. However, in the RFID field the usable frequencies of operation are strictly controlled and are limited. The U.S. FCC, and other national authorities around the world, have established regulations that define the frequency bands in which wireless systems (RFID, WiFi™, Bluetooth, etc.) can operate license free. The UHF band in the U.S. extends from 902.5 MHz to 928.0 MHz and was selected for RFID technology because of the low attenuation of this frequency in free space (i.e., it provides the longest read distance and therefore is ideal for supply chain management). It has been found that enclosures are desired for the storage of certain articles that do not have a resonant frequency matching one of the allowed RFID frequencies. Thus, a robust EM field must be established in another way.

Once activated, the RFID tags transmit their respective identifications that are received by a receive antenna and conducted to an RFID reader to determine their presence in the container. This is commonly referred to as reading the RFID tag. In order to read the tags, an injection probe or probes are placed within a storage cabinet along with a receive antenna or antennas. In another embodiment, the injection probe and receive antenna are the same device and both functions are accomplished by switching the device between an energy injection mode and an energy receive mode. The receive antennas are interfaced with the RFID reader, which can be permanently mounted at the cabinet. The system sends activating energy, also known as interrogation signals, via the injection probe which emits that activating energy in the storage container. The activating energy is strong enough (also described as having a high enough power level) to activate the passive RFID tags. Those activated tags then respond with their stored data. The receive antennas receive the responsive data from the RFID tags and this data is forwarded to the RFID reader.

In the healthcare environment, cabinets enabled with RFID tracking systems employ a Faraday cage, which is a conductive chamber completely surrounding the container area. The Faraday cage prevents the RFID tracking system located inside the container from reading RFID tags outside the container area which would cause an error. The Faraday cage also preserves the RF energy within the enclosure for use in identifying RFID tags.

Various problems exist with RFID tag activation in an enclosed space. As discussed above, there are often nulls or dead spaces or dead zones in which tags will not receive enough RF activating energy to be activated. Placing many RFID activation probes throughout the enclosed container will increase the chances of activating all RFID tags, but at the cost of more wires, probes, and antennas. Use of a large quantity of antennas also results in larger enclosures and increased read process time. Increasing the power level in the container may help but there are limits imposed by FCC on the power level. For example, in the U.S., a maximum transmit power of 4 watts (EIRP—equivalent isotopically radiated power) is allowed. Additionally, power levels that are too high may increase the chances of reading RFID tags located outside the container even though the Faraday cage exists. It has been found that Faraday cages used as containers that must allow access may leak the activation energy outside the container and the tracking system may detect RFID tags on medical articles located outside the container thereby causing a tracking error.

Another problem is the effect that liquids have on an RFID reader. Liquids may actually absorb the activation energy resulting in the failure to activate an RFID tag. Other errors are caused by tags next to each other (tags positioned in close proximity to or directly against one another) detuning each other such that they are not activated by the RF activation field. Many such conventional designs can suffer from poor results obtained due to the static nature (tag positions are fixed) of the interrogations. In an application where the field is static, a tag may lie in a RF null created by multipath, resulting in a failed interrogation.

Further, many conventional solutions use the traditional combined transmit/receive antenna configuration. In this arrangement, a single wireless EM conduction device operates as both a transmit antenna and as a receive antenna. This configuration works well in traditional applications where the RFID reader antenna radiates into open space and objects are in the far-field region of the antenna for minimum RFID reader antenna detuning. Far-field is described as a boundary region where the angular field distribution of the antenna is essentially independent of distance from the source. However, in applications where the RFID tags to be read are in the interior space of a container that is within the near-field of the transmitting device, problems can arise. Reflections of the transmitted energy can establish the null zones within that container. For purposes of discussion herein, the wireless EM conduction device for the interior of a container is referred to as an "injection probe" because it is injecting activating RF energy into a closed space. In a case such as this, i.e., where the target space is closed, the traditional combined transmit/receive antenna approach and combined transmit and receive systems can encounter problems in activating an RFID tag that falls within a null zone.

As RFID tagged products enter the RFID reader antenna's near-field region, it has an adverse effect on the RFID reader's antenna tuning resulting in reduced RFID reader receiver sensitivity. This results in RFID reader antenna detuning and presents a challenge for the RFID reader's receiver in terms of energy reflected back into the RFID reader receiver competing with energy reflected back by the tagged items. Still further, RF signal propagation in contained environments is not well defined, with huge amplitude variations in resonant versus null locations within a drawer or chamber. When RFID tags are placed in a chamber's null locations, the tags cannot be powered and cannot be read/interrogated, ultimately causing errors in tracking medical articles.

Another problem exists when a tag is in its minimum field strength (such as between two transmitting antennas) with respect to its ability to turn on and participate in the interrogation. When this occurs the RFID reader may be unable to detect the tags' faint responses resulting in a failed interrogation. This is a common problem in a high product/tag density application where high concentration of items exists within the RF Tx and Rx paths. A similar problem with conventional solutions occurs when the items being tracked include large amounts of liquids. Conventional RFID cabinet systems typically use the electric field to communicate to passive RFID tags. Depending on the frequency used, some frequencies can be greatly attenuated by liquid items within the container resulting in a failed interrogation due to insufficient field strength. To lessen such effects, some manufacturers use larger RFID tags so that they will be more immune to detuning caused by a large number of tags located near each other. Also, it is thought that larger tags somewhat overcome the detuning of liquids. However, larger tags result in difficulty of handling the medications. This is discussed further below.

The above cause great difficulties for those RFID systems that are designed and developed to track RFID tags on items in the near field (distances less than approximately one wavelength from the antenna). The wavelength for electromagnetic energy of 915 MHz is 12.91 inches (32.77 cm), which is typical for RFID-enabled enclosures employed for storing medication, such as drawer systems, metal cabinets, refrigerators, and freezers. Integrating antenna systems in metallized or shielded enclosures used for tracking stored items tagged with RFID tags or smart labels, such as refrigerators, freezers, drawers, cabinets, etc., presents challenges due to the large amounts of energy that reflect off the enclosure walls and any metallized element inside the enclosure. Irrespective of energy reflections inside of a metallized enclosure it is difficult to set up electromagnetic waves in volume-restricted metallized enclosure, especially those enclosures that are non-resonant at the frequency of interest.

FIG. 3 shows what is called an RFID "flag" tag. The tag, which has commonly been in use for many years, includes a "flag" portion 72 on which is mounted an RFID device 76, and a mounting portion 74 that comprises a clear base on which a layer of clear adhesive is deposited. The mounting portion is adhered to the vial of medication for example. Because the mounting portion is clear, the label 75 placed on the vial by the manufacturer can be read through the mounting portion thus not obscuring expiration dates, dose size, name of the medication, name of the patient, and any other data placed on the vial. The commonly-used flag tags that are relatively large and consequently unwieldy. They take up excessive space in a storage container, interfere with each other during handling, and are difficult to handle. These more common tags are in widespread use because they contain a much larger RFID tag coupling device (antenna). This is necessary for many manufacturers of tracking systems because the larger-sized RFID tag coupling devices are able to collect more activating RF energy in those tracking systems that are inefficient and have dead zones or "weak zones." FIG. 4 on the other hand shows the smaller-sized RFID flag tags that are preferable. Medications on which such smaller-sized tags are mounted are easier to handle, take less room, and are easier to store in containers. Even though the users of RFID tracking systems prefer the smaller RFID tags, many manufacturers cannot use them because they will not be activated with their RFID tracking systems and tracking errors will result.

Typical antennas used in RFID applications are microstrip antennas, patch antennas, and wire-based antennas. Although these types of antennas perform well for far field applications, they can generate null areas or regions, or low power (weak) areas or regions of activating RF energy at localized points in the near field due to the large aperture or effective area of the antenna. In addition, these antennas radiate an energy wave that is more linear than circular, which can result in loss of RFID tag interrogation energy due to the tag being cross polarized when positioned in the near field.

Tracking small form factor medications in small non-resonant enclosures requires smaller RFID tag sizes in order for the tagged items to fit easily into a tray or drawer pockets without impeding the loading of medications, dispensing of medications, or the opening and closing action of the drawer, container, or enclosure in which the medications are stored. Certain small form-factor RFID tags that operate in the 915 MHz industrial, scientific, and medical ("ISM") radio bands include both a magnetic antenna loop/feature and a folded dipole so that both magnetic and electrical field energy can be harvested to operate the RFID tag. By definition, the RFID tags attached to small medication form factors stored in small non-resonant enclosures will be in close proximity (near field at 915 MHz) to the activating RF energy injection probes.

Certain antennas do not perform well under the difficult conditions of a relatively small container. For example, thin profile microstrip antennas have narrow bandwidth and poor radiation efficiency with a lossy substrate and therefore these planar patch antennas are not a good choice for a low cost solution. Additionally, a relatively large size of a microstrip antenna is required for performance at a frequency of around 900 MHz which makes it undesirable in most applications where space is at a premium.

Hence, those of skill in the art have identified a need for using a much smaller RFID flag tag on medical articles to be stored in a container, for using less power to activate all RFID tags in a container, and for having a much higher success rate of tag activation and reading. The present invention fulfills these needs and others.

SUMMARY OF THE INVENTION

Briefly and in general terms, the present invention is directed to a system and method for activating and reading RFID tags located in non-resonant enclosures using a hybrid IMD probe to inject electromagnetic energy ("EM") for powering and interrogating the RFID tags. The IMD probe can be employed as a passive injector of EM or combined with dynamic impedance matching and/or beam steering capability.

In accordance with an aspect of the invention, a probe is provided having a capacitively-loaded inductive loop that sets up a magnetic dipole mode and provides a magnetic near field that is as strong or stronger than the electric near field. Another aspect is that the capacitively-loaded loop effectively provides a self-resonant structure that is decoupled from the local environment.

In an additional aspect, a probe is provided with an RFID reading system that comprises a capacitively coupled inductive loop causing electrical currents to be strongly localized in the probe region and thereby not propagating to the ground. Fringing electrical currents are minimized resulting in a large magnetic near field component that is much more likely to activate RFID tags within the radiation field of the probe.

In other aspects, there is provided a tracking system for tracking medical articles stored in the interior volume of a container, the interior volume of the container having a size selected to receive a plurality of medical articles each of which has a wireless identification device associated therewith that has individual identification data, and each wireless identification device configured to respond with identification data upon receiving activation energy, the interior volume of the container having a resonant frequency that is different from a frequency of operation of the wireless identification device, the system comprising, electromagnetic shielding ("EM") located about the interior volume of the container, an electromagnetic energy conducting probe located within the EM shielding, the probe having a radiation pattern directed to the interior volume of the container, wherein the probe comprises a main conductive element having capacitive coupling across at least one slot of the main conductive element thereby forming an isolated electric field that fills the interior of the container, and wherein the main conductive element is spaced apart from a ground plane by a selected distance thereby forming a robust magnetic field that is orthogonal to the electric field and that also fills the interior of the container, a signal source producing activating RF energy having a frequency that is different from the resonant frequency of the interior volume of the container, and coupled to the probe, and a processor connected with the signal source, the processor being programmed to control the signal source to deliver RF energy to the probe for injecting into the interior of the container to activate identification devices in the interior, the processor further being programmed to stop the signal source from delivering RF energy to the probe to allow the probe to receive identification signals from activated identification devices in the interior.

In accordance with further aspects, the probe comprises a hybrid isolated magnetic dipole device in which the electric and magnetic fields are circularly polarized. The probe includes a parasitic element located at a selected position in relation to the main conductive element such that the parasitic element alters the direction of the radiation pattern. The probe includes a controllable active tuning element connected with the parasitic element to alter the effect of the parasitic element on the main conductive element to controllably change the direction of the radiation pattern.

In yet a further aspect, the medical article tracking system further comprises a dual probe circuit in which a plurality of probes are co-located and positioned in relation to each other to provide multiple radiation patterns into the interior volume.

In an additional aspect, the medical article tracking system further comprises an active tuned impedance matching circuit connected with the probe that controls impedance of the probe to more closely match the impedance of the interior volume of the container whereby increased efficiency in electromagnetic energy transfer into the interior of the container results.

In accordance with method aspects, there is provided a method for tracking medical articles stored in the interior volume of a container, the interior volume of the container having a size selected to receive a plurality of medical articles each of which has a wireless identification device associated therewith that has individual identification data, and each wireless identification device configured to respond with identification data upon receiving activation energy, the interior volume of the container having a resonant frequency that is different from a frequency of operation of the wireless identification device, the method comprising shielding the interior volume of the container from the passage of electromagnetic ("EM") energy, injecting activating RF energy into the interior volume in a radiation pattern with a probe that comprises a main conductive element having capacitive coupling across at least one slot of the main conductive element thereby forming an isolated electric field that fills the interior of the container, and wherein the main conductive element is spaced apart from a ground plane by a selected distance thereby forming a robust magnetic field that is orthogonal to the electric field and that also fills the interior of the container, delivering activating RF energy to the probe from a signal source, the activating energy having a frequency that is different from the resonant frequency of the interior volume of the container, and controlling the signal source to deliver the activating energy to the probe for injection into the interior volume, and controlling the signal source to stop delivering activating energy to the probe so that the probe may then receive responsive identification signals from activated identification devices.

The features and advantages of the invention will be more readily understood from the following detailed description that should be read in conjunction with the accompanying drawings.

DETAILED DESCRIPTION OF THE PREFERRED EMBODIMENTS

Figure 1:
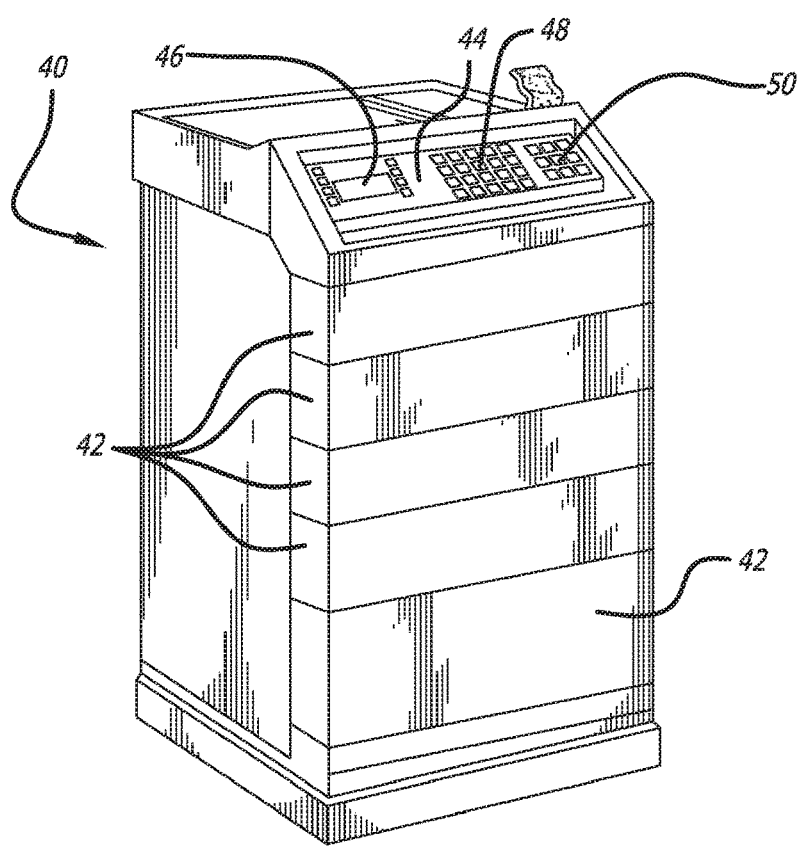
FIG. 1 is a view of an automated dispensing cabinet ("ADC") having multiple drawers in which articles are stored, the ADC having an article tracking system and a built-in computer configured for tracking the stored articles by processing data regarding articles put into the ADC and removed from the ADC, and communicating over one or more networks.

Referring now in more detail to the exemplary drawings for purposes of illustrating embodiments of the invention, wherein like reference numerals designate corresponding or like elements among the several views, there is shown in FIG. 1 a representative medical dispensing cabinet 40 also known as an automated dispensing cabinet ("ADC") 40. The ADC comprises a plurality of movable drawers 42. In this embodiment, there are five drawers that slide outwardly from the cabinet to provide access to the contents of the drawers. Each drawer may be thought of as a container having an interior volume in which medical articles may be stored. The cabinet also comprises an integral computer 44 that may be used to control access to the drawers and to generate data concerning access to and contents of the drawers, and to communicate with other systems. In this embodiment, the computer generates data concerning the number and type of items in the drawers, the names of the patients for whom they have been prescribed, the prescribed medications and their prescribed administration dates and times, as well as other information.

In an embodiment, the ADC 40 comprises an RFID tracking system that tracks the contents of the drawers by activating RFID tags attached to the contents. The computer 44 may receive unique identification numbers from the RFID tags attached to the stored items and pass those identification numbers to an inventory control computer that has access to a database for matching the identification numbers to item descriptions, or perform those steps itself. The ADC of FIG. 1 also includes a user interface comprising a display 46, a typing keyboard 48, and a keypad 50. In another embodiment, the computer 44 contains a database and is capable of displaying the name of the medical article, the dose, the patient name for which it was prepared, and other data/information on the display and may accept commands from the user interface.

As used in regard to the embodiments herein, "tag" is meant to refer to an RFID transponder. Such tags typically have a coupling element, such as an antenna, and an electronic microchip, also referred to as an integrated circuit ("IC"). The IC includes data storage, also referred to as memory.

A cabinet exemplified by the ADC 40 of FIG. 1 may be located at a nursing station on a particular floor of a health care institution and may contain prescriptions for the patients of that floor. As prescriptions are prepared for the patients of that floor, they are delivered and placed into the cabinet 40. They are logged into the integral computer 44, which may notify the pharmacy of their receipt at the cabinet. A drawer 42 may also contain non-prescription medical supplies or items for dispensing to the patients as determined by the nursing staff or physicians. At the appropriate time, a nurse would access the drawer in which the medical items are stored through the use of the computer 44, remove a particular patient's prescriptions and any needed non-prescription items, and then close the drawer so that it is secured. In order to access the cabinet, the nurse may need to provide various information and may need a secure access code. The drawers 42 may be locked or unlocked as conditions require.

In another embodiment, the drawers may be unlocked and accessible at any time by any one as desired. In another embodiment, one or more drawers may contain controlled substances, such as narcotics, and must be locked. In a further embodiment, all drawers, or no drawers, or only select drawers may be refrigerated.

The computer 44 in some cases may be in communication with other facilities of the institution. For example, the computer 44 may notify the pharmacy of the health care institution that a patient's prescription has been removed from the cabinet 40 for administration at a particular day and time. The computer may also notify the finance department of the health care institution, and/or other entities, of the removal of prescriptions and other medical items for administration to a particular patient. This medication may then be applied to the patient's account. Further, the computer 44 may communicate to the institution's administration department for the purpose of updating a patient's Medication Administration Record (MAR), or e-MAR. The computer 44 of the medication cabinet 40 may be wirelessly connected to other computers of the health care institution or may have a wired connection. The cabinet may be mounted on wheels and may be moved about as needed or may be stationary.

Although not shown, each of the five drawers of the ADC 40 contains a door, or drawer, sensor that detects when the respective drawer is opened. A door-open signal is generated and received by the integral computer 44 of the ADC. The signal is stored in a database along with the time of receipt for possible future reference. The same sensor or a different sensor may detect when the drawer is closed and generates a door-closed signal.

Figure 2:
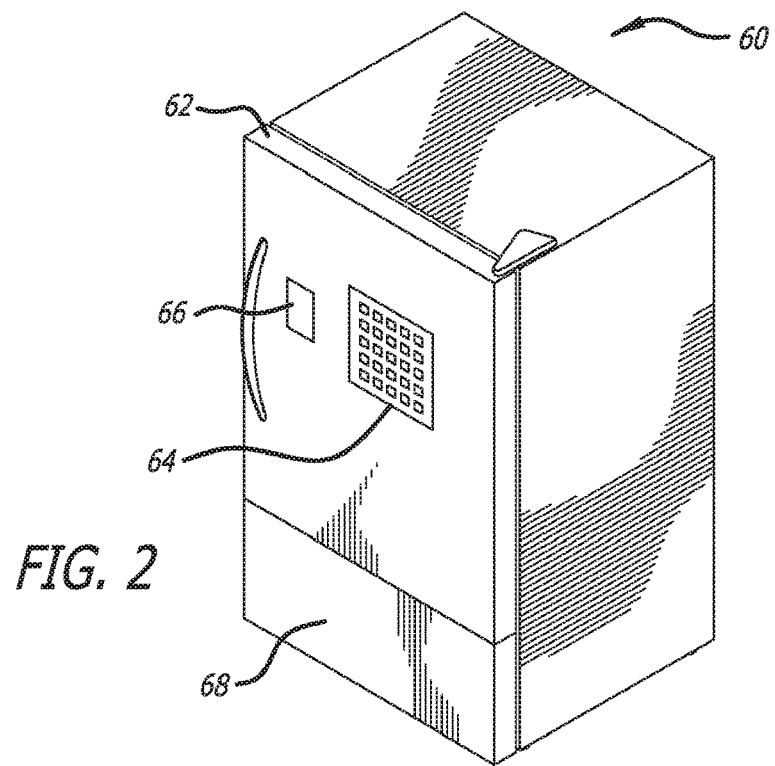
FIG. 2 is a view of a 2.3 ft$^3$ refrigerated cabinet in which medical articles are stored, and tracked, the cabinet in this case having a keypad and a display on the front door for interfacing with the programming of a processor in the cabinet.

FIG. 2 presents a different type of cabinet container 60. In this embodiment, the cabinet is a refrigerator having a small size, such as 2.3 cubic ft ($ft^3$). In this embodiment, the front door 62 includes a keypad 64 and a display 66, as well as a handle to control whether the door is open or closed. The lower section 68 includes a processor, the RFID electronics, as well as communication electronics, power control, and any additional processors that may be needed. Although this embodiment shows a small refrigerator having a display and keypad, they are not necessary to the invention. The refrigerator 60 may have no user interface and the RFID tracking system of the refrigerator may automatically track the contents of the refrigerator and automatically communicate the results to a remote computer, or smartphone, or other device.

Figure 3:
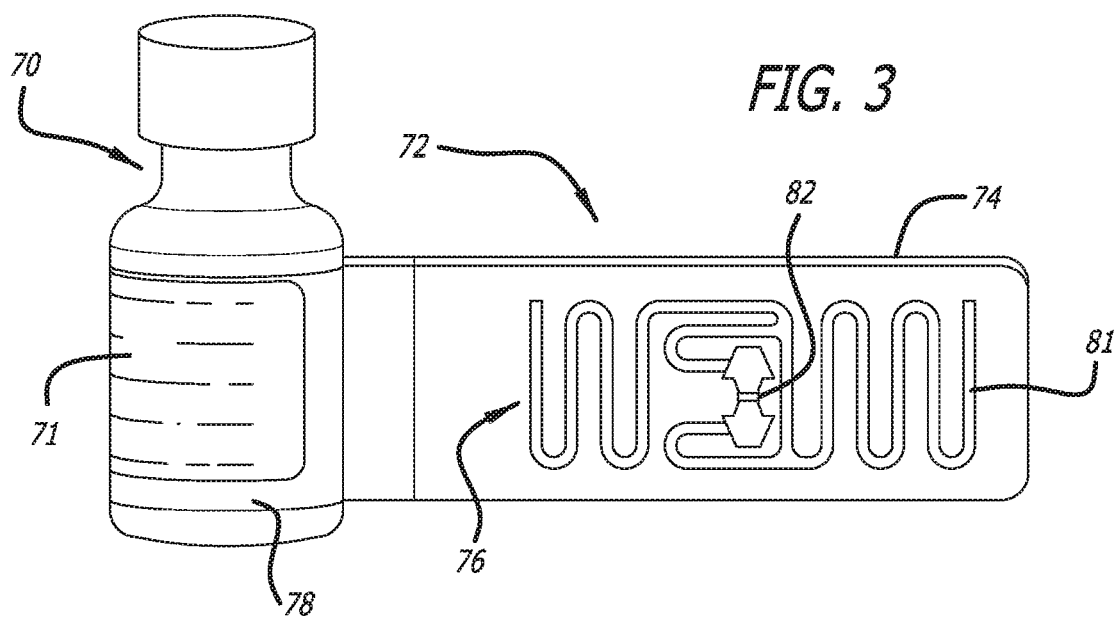
FIG. 3 is a view of a medication vial having a commonly-used RFID "flag tag" attached thereto, the flag tag in this diagram has a relatively large size that makes the vial bulky and can interfere with the handling of articles and storing the articles in a container.
Figure 4:
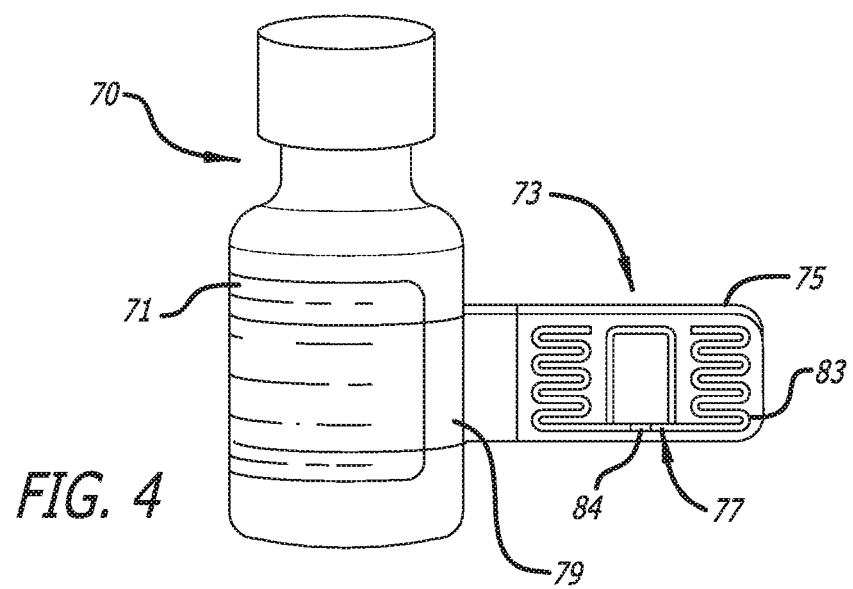
FIG. 4 is a view of the same medication vial of FIG. 3 but in this figure, a compact RFID flag tag is attached, the compact flag tag being much smaller than that of the previous figure due to the smaller size of the RF energy coupling device used in the RFID tag mounted thereon.

FIGS. 3 and 4 present views of different RFID "flag-tags" 72 and 73 in use today. Both are attached to medical vials 70 that have the same size. The medical vial in both figures also have the same label 71 attached to the vial, on which is written various information about the contents of the vial, such as the name of the drug in the vial, the dose, the quantity, the expiration date, the manufacturer, the prescribing physician, and possibly more information or less information. The "flag tags" of FIGS. 3 and 4 are given this name because they include a length of paper 74 and 75 respectively or a "flag" portion upon which an RFID tag 76 and 77 respectively is mounted, and a mounting portion comprising a length of a clear attachment strip 78 and 79, having a clear adhesive, that is placed over the vial's label 71 to attach the flag tag to the vial 70. The mounting portion comprising the attachment strip and adhesive may be a tape material and are clear so that any information written on the label 71 of the vial 70 can be read through the mounting portion even though the respective flag tag is attached.

In FIG. 3, the RFID flag-tag 72 is a typical size in use today as discussed previously, which is relatively large. The reason for the large size of the flag-tag is so that it can mount an RFID tag 76 that has a large coupling element 81 or antenna. The coupling element must be large enough to receive and collect an operational amount of activation RF energy to activate the RFID integrated circuit 82 of the RFID tag 80. Such large RFID tags are used on medical articles that are to be stored in containers having RFID tracking systems that do not provide a robust RF energy activation field. This field may also be referred to herein as an interrogation field or a reading field. Thus the coupling element 81 for RFID tags used in an environment such as this must be larger to collect more RF energy to activate the RFID tag 76.

On the other hand, the RFID flag-tag 73 of FIG. 4 is much smaller than that of FIG. 3. This is due to the coupling element 83 or antenna of the RFID tag 77 of FIG. 4 being much smaller. The integrated circuit 84 of the RFID tag of FIG. 4 is approximately the same size as the integrated circuit 82 of the RFID tag 80 of FIG. 3. With an RFID tag 77 of the type of FIG. 4, a much stronger RF activating energy field must surround the RFID tag to activate it. RFID tracking systems that are designed with more efficient energy transfer, such as provided by the present invention, can successfully operate with the smaller sized RFID tags as shown in FIG. 4 and still produce a one-hundred percent read rate (also referred to as "interrogation rate," "activation rate," "detection rate," and possibly other names). The advantage of using the smaller tags of FIG. 4 is that they take less room in a container, do not visibly obscure the existence of other medical articles, so not interfere with each other, and are easier to handle.

Figure 5:
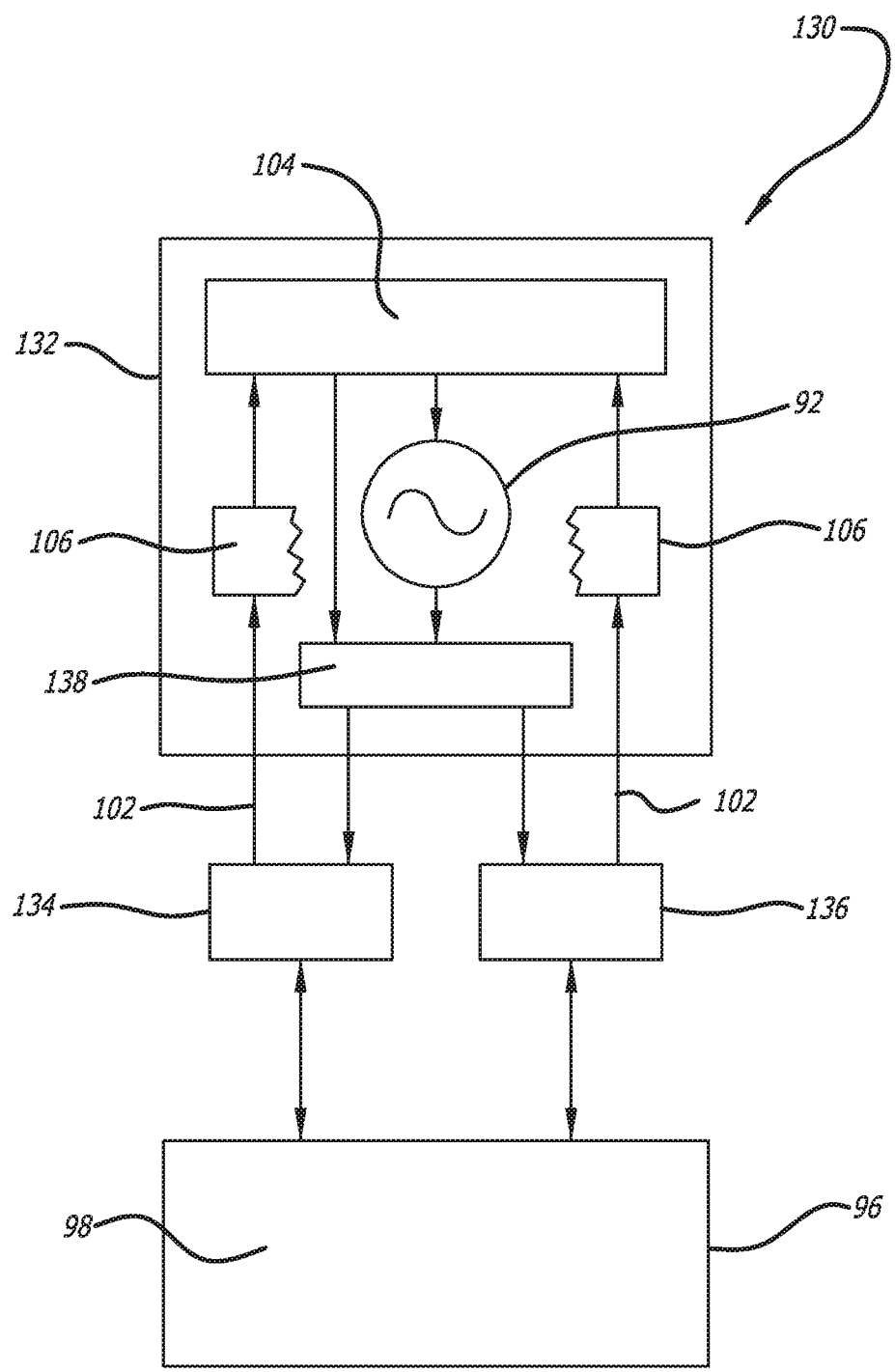
FIG. 5 is a schematic block diagram of an RFID tracking system comprising an RFID reader positioned for scanning the interior of an article storage container, and having two separate RF energy conducting devices acting in one mode as RF probes for injecting activating RF energy into the container, and operating in a second mode as RF probes for receiving the RF responses of the activated RFID tags attached to articles stored in the container, the RF probes connected to conduct the RFID tag responses through a receiver to extract data and then to the processor of the RFID reader for further processing; the processor of the reader also programmed for frequency control over the signal generator for providing frequency hopping and timing control of the activating RF energy injected into the storage container by the RF probes.

FIG. 5 provides an RFID tracking system 130 in accordance with aspects of the invention in which an RFID reader 132 provides activating RF energy with a signal generator 92 to two RF energy conduction devices 134 and 136 that both operate in one mode as RF energy injection probes that provide activating RF energy to a container 96 interior 98. This activating energy activates RFID tags in the interior of the container which then respond with RF identification data. In this embodiment, the same EM energy conduction devices 134 and 136 also operate in a second mode as receiving probes that receive the responses of the activated RFID tags that are present in the container and that have been activated by the activating RF energy. The receiving probes 134 and 136 communicate those responses 102 to the RFID reader's receiver 106. The receiver is shown broken in this figure for the purpose of clarity in the figure. In this embodiment, it is a single receiver that extracts the identification data from the RF response signals of the activated RFID tags in the interior 98 of the container 96 and communicates that identification data to the processor 104. In another embodiment, multiple receivers may be used. Thus in this embodiment, the RF energy probes 134 and 136 operate wirelessly as both an energy injection probe and as a receiving probe.

The system of FIG. 5 also comprises an RF energy conduction device switch 138 for selectively switching the RF probes 134 and 136 to either injection mode or receive mode as desired. Also, the processor 104 of the RFID reader 132 has been programmed for frequency control over the signal generator 92 for providing frequency hopping of the activating RF energy injected into the storage container 96.

The term "probes" has been adopted for the energy transfer devices in this disclosure, as opposed to the word "antenna," because the energy transfer device or devices are injecting and receiving EM energy from a cavity, which in this disclosure has been termed a "container."

Figure 6:
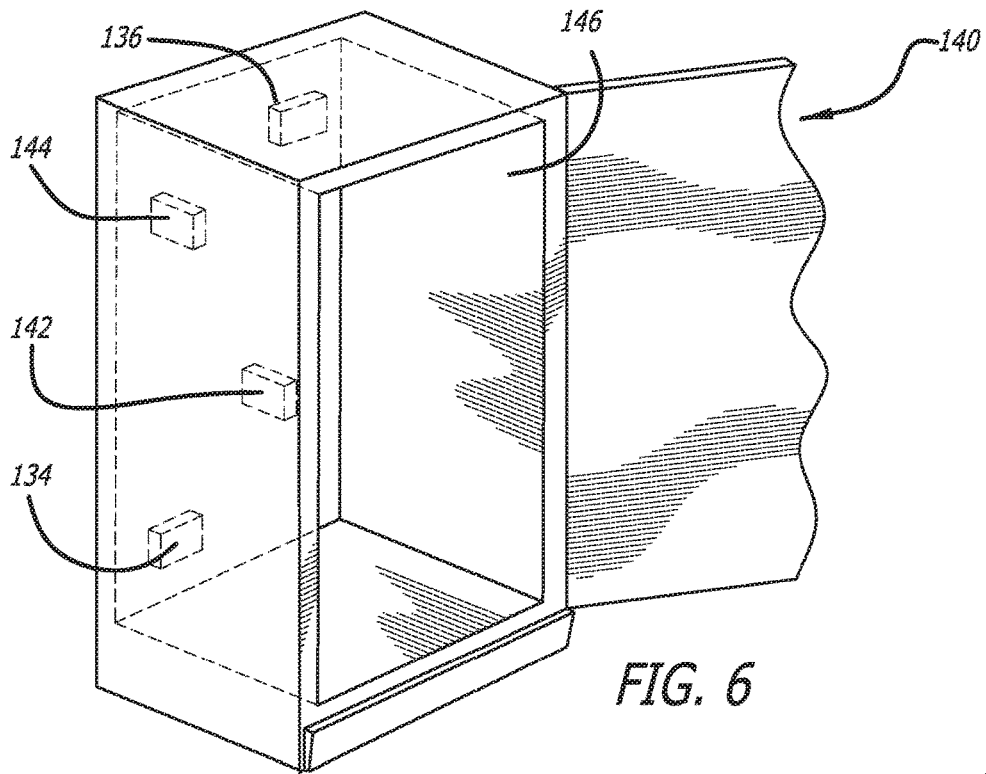
FIG. 6 is a perspective view of a larger refrigerated cabinet, in this case a 12 ft$^3$ cabinet, with the front door open showing an embodiment of the placement of multiple RF probes in the cabinet for tracking medical articles put into, stored, and taken out of or removed from the cabinet.

FIG. 6 is a view of a much larger storage container 140, in this case a 12 ft$^3$ refrigerated cabinet. Although not shown in the figure, medical articles may be stored in this refrigerator. Shelves have also been removed for clarity of the figure. A total of four RF probes 134, 136, 142, and 144 are mounted in the refrigerator interior 146 to scan the entire interior volume of the cabinet. FIG. 6 shows the particular placement of multiple probes in a 12 ft$^3$ refrigerator; however, in another embodiment more or fewer such devices may be used depending on the circumstances and they may be placed in different locations. In this case, the four devices are mounted with two 134 and 136 on the back wall and two 142 and 144 on the left wall. The location of the RF energy conduction devices may also vary depending on particular circumstances of the container shape, size, and the type of RFID tags used.

The performance of RFID tags will vary from one design to another. "Read performance" can be defined by a variety of RFID tag characteristics: read distance of a single tag in free space, probe polarization (linear or circular), sensitivity to adjacent tags, sensitivity to metal in close proximity, sensitivity to liquids in close proximity, sensitivity to detuning from packaging materials, location of the RFID tag in the enclosure, but also the orientation of the RFID tag, proximity of the tag to the enclosure walls and the drawer material (surfaces), among others. All of the above performance characteristics affect the statistical probability that a tag can be identified in an RF-enabled enclosure with multiple probes. In addition to variations in performance between differing tag designs, performance can also vary from one tag to another of the same design. Variations in the tag assembly process, the tag antenna material, and possibly the integrated circuit ("IC") characteristics can result in performance variation within a group of one tag type/design.

What has been needed, but not available, is an RF energy injection probe that can overcome the above sensitivities and performance-degrading conditions so that all RFID tags in the interior of a container are activated. A device satisfying this need has been found to be a hybrid isolated magnetic dipole ("IMD") probe. The hybrid IMD probe has been found to provide superior efficiency, isolation, and selectivity characteristics and has a relatively small size due to the configuration of the elements used. The hybrid IMD probe excites a magnetic dipole mode from a metal structure in such a fashion as to minimize the fringing fields typically generated between a probe element and an adjacent ground plane. A current is induced on the probe structure and a strong electric field is generated on the structure in the plane of the IMD element instead of a strong fringing field to the ground plane. By minimizing the coupled fields to the ground plane, with the circuit board of a wireless device taking the place of the ground plane, improved efficiency and isolation can be obtained. Single and multi-resonant elements can be created to address a wide range of frequency bands.

The hybrid IMD probe confines current flow on the probe main conductive element and thereby optimizes the isolation. Near-field emissions are controlled. Other probe designs have strong current flows radiating out onto their ground plane board and lose large amounts of energy resulting in lower probe efficiency. The hybrid IMD probe design provides a solution for accurately and repeatedly identifying RFID tags attached to both large and small medication form factors in small non-resonant RF-enabled enclosures. RFID tag interrogation performance in a non-resonant cavity can be improved by using the hybrid IMD probes disclosed here instead of electric probes or magnetic loops or half loops. The near-field magnetic properties along with high cross polarization characteristics of the hybrid IMD probe main element provide unique capabilities when the hybrid IMD probe is used as an energy injection probe in the cavity. The improvement from using hybrid IMD probes as injection probes in the non-resonant cavity compared to typical electric or magnetic probes is due to the ability of the hybrid IMD probe to act as a magnetic and electric field probe simultaneously as a result of the high cross polarization of the IMD main element.

The hybrid IMD probe is formed by coupling one element to another in a manner that forms a capacitively-loaded inductive loop, setting up a magnetic dipole mode. This magnetic dipole mode provides a single resonance and forms a probe that is efficient and well isolated from the surrounding structure. This is, in effect, a self-resonant structure that is de-coupled from the local environment.

The hybrid IMD probe involves placing a conductor in close proximity to a slot or conductive regions of an IMD probe to create a reactive section capable of increasing the bandwidth of the IMD probe. The conductor can be capacitively coupled to the IMD probe or can be connected to a portion of the IMD probe. Lumped reactance in the form of capacitors and/or inductors can be incorporated into the probe structure, to both the driven element and/or the coupled element, to provide additional adjustment to the frequency response. Increases in both efficiency and bandwidth have been documented from this technique which more efficiently utilizes the volume that the probe occupies.

Figure 7:
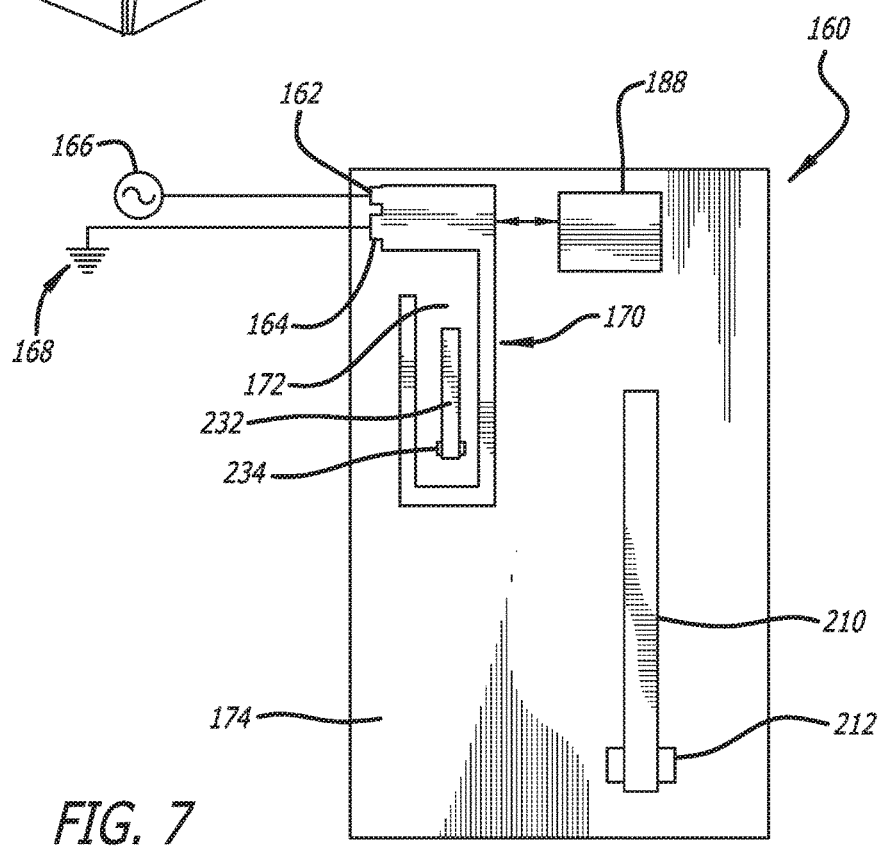
FIG. 7 is a top view of a hybrid isolated magnetic dipole ("IMD") probe used for injecting activating RF energy into a container to activate RFID tags stored therein to respond with their individual identification data, the hybrid IMD probe having a single main element conductor located parallel to and distanced away from a circuit board with at least one slot in the single conductor for capacitive coupling that establishes a robust, but isolated, electric field in a container, and the spacing of the single main element above the circuit board to also establish a robust magnetic field in a container, a dynamic impedance matching device is shown located next to the main element and connected thereto for matching the impedance of the main element to the impedance of the container, and two parasitic elements.

A first type of hybrid IMD probe (Type 1) 160 as shown in the top view of FIG. 7 comprises a pair of conductors 162 and 164 placed in close proximity to each other with portions of each conductor positioned in parallel with each other. One conductor 162 is connected to a signal source 166 and a second conductor 164 is grounded 168 on one end. The overall structure of the main element 170 can be considered as a capacitively-loaded inductive loop. The capacitance is formed by the coupling between two parallel conductors 162 and 164 with the inductive loop formed by connecting the second element 164 to ground 168. The length of the overlap region between the two conductors along with the separation 172 between conductors is used to adjust the resonant frequency of the probe 160. A wider bandwidth can be obtained by increasing the separation between the conductors, with an increase in overlap region used to compensate for the frequency shift that results from the increased separation. This type of hybrid IMD probe requires a ground plane 174 for operation. With a ground plane 174 coupled to the IMD probe 170, this hybrid IMD probe can be considered a half-loop radiator, providing a strong magnetic field component in the near-field of the probe as well as a strong electric field.

Also shown in FIG. 7 is an active impedance matching circuit 188 in block form. The main element 170 of the IMD probe 160 is connected with the matching circuit to vary the impedance of the IMD probe to a value as close to the impedance of the container with which it is associated as possible so that energy is efficiently transferred between the two. Such impedance matching circuits are known in the art. See U.S. Pat. No. 8,384,545 to Hussain et al., incorporated herein by reference, for a description of such a circuit usable here.

Figure 8:
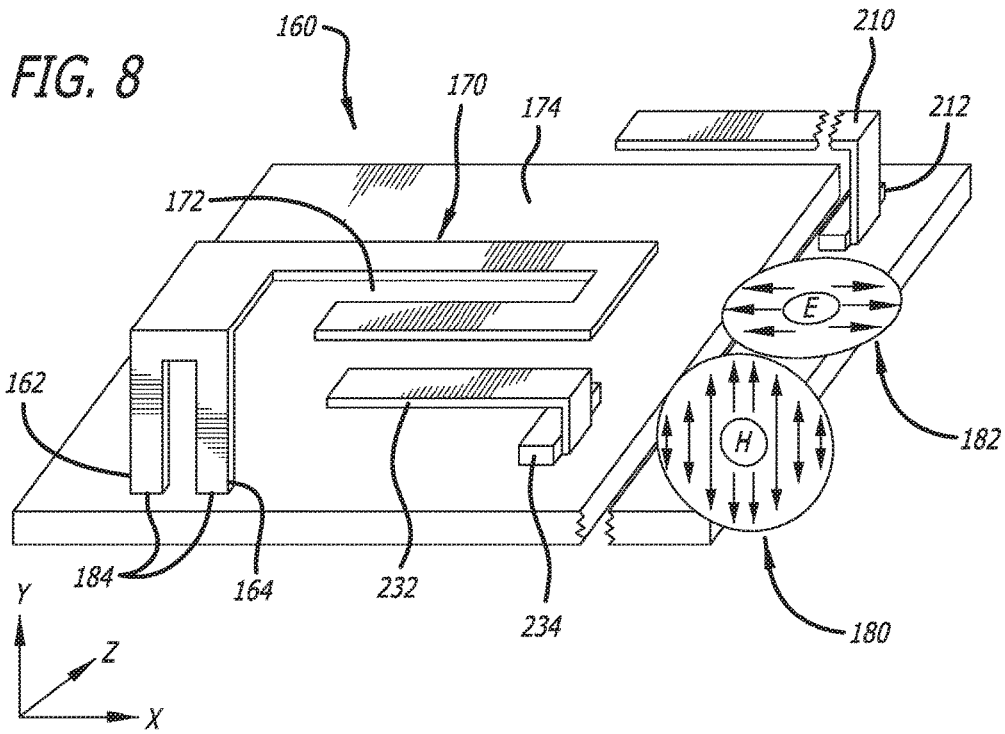
FIG. 8 is a perspective view of the hybrid IMD probe of FIG. 7 depicting the electric near field and the magnetic near field created by the probe, further showing the relative locations of the parasitic elements in relation to the main conducting element of the probe, wherein the parasitic element located beside the main element functions to steer the radiation pattern of the probe.

FIG. 8 shows a perspective view of the IMD probe 160 of FIG. 7 and further shows the magnetic field "H" 180 and the electric field "E" 182 created by the IMD probe. It will be noted that the electric field "E" is in the X plane while the magnetic field "H" is in the orthogonal Y plane. Both fields are robust and fill the entire interior of a container 60 such as that shown in FIG. 2.

An advantage of this hybrid IMD type of probe structure is the method in which the probe is fed or excited. This leaves great flexibility for reduced-space integration. The probe size reduction is obtained by the capacitive loading that is equivalent to using a low loss, high dielectric constant material. At resonance a cylindrical current going back and forth around the loop is formed. This generates a magnetic field "H" 180 along the axis of the loop which is the main mechanism of radiation. The electrical field "E" 182 remains highly confined between the two elements 162 and 164. This reduces the interaction with surrounding metallic objects and obtains high isolation.

In accordance with one aspect of the invention, the hybrid IMD probe 160 of FIGS. 7 and 8 provides high energy efficiency. The hybrid IMD probe comprises a capacitively-coupled inductive loop 170 where multiple components of a part of the loop are capacitively coupled together to create a robust electric field and the inductive coupling of the components to the ground plane create an equally robust magnetic field. FIG. 8 provides a perspective view of an IMD main element 170 situated above a ground plane 174. The ground plane 174 may include an impedance matching circuit 188 incorporated therein. The main element of the probe 170 consists of a slot region 172 and prong type feed and ground legs 184. A current is induced around the U-shaped probe structure 170 through a feed port and ground of the wireless device. The current is induced in order to generate a strong electric field in the slot region, in the plane of the IMD element 170 instead of a strong fringing field to the ground plane 174 below it. This minimizes the coupled fields to the ground plane 174. With a circuit board of a wireless device acting as the ground plane, an improved efficiency and isolation may be obtained. Different configurations of these resonant elements may be made in order to address a wide range of frequency bands.

The length of the IMD element 170 may be modified to be longer or shorter dependent on the frequency desired. For instance, longer IMD elements 170 show improved lower frequency ranges. In addition the center slot capacitive region 172 may be wide or narrow. In addition multiple slot regions may be formed, as is provided in FIG. 13. The height of the IMD element 170 above the ground plane 174 also affects the frequency range functionality of the probe. By displacing the portions of the structure in three dimensions, the IMD element can be optimized at various frequency regions. Lower frequencies will be more efficient when implemented with increased height, such as 6 mm, while higher frequencies will be more efficient with lower heights, such as 4 mm. As well, the height above the ground plane for optimal efficiency varies as probe operation varies from 1800 MHz to 2200 MHz. Discrete steps in height are applicable, as well as variable and continuous increases or decreases in element height as a function of element length. For further details on modifying an IMD probe, refer to U.S. Pat. No. 7,777,686, incorporated herein by reference.

The embodiment of a hybrid IMD probe shown in FIGS. 7 and 8 comprises an isolated main probe element 170, a first parasitic element 210, and a first active tuning element 212. The first parasitic element 210 and its associated first active tuning element 212 are positioned to one side of the main probe element. In one embodiment, the first active tuning element is adapted to provide a split resonant frequency characteristic associated with the probe 170. The first active tuning element may be adapted to rotate the radiation pattern associated with the IMD probe 160. This rotation may be effected by controlling the current flow through the parasitic element 210. In one embodiment, the first parasitic element 210 is positioned on a substrate 174. This configuration may become particularly important in applications where space is the critical constraint. In one embodiment, the parasitic element is positioned at a predetermined angle with respect to the main probe element 170. For example, the first parasitic element 210 may be positioned parallel to the main probe element 170, or it may be positioned perpendicular to the main probe element. The parasitic element may further comprise multiple parasitic sections.

In one embodiment of the present invention, the first active tuning element 212 comprises at least one of the following: voltage controlled tunable capacitors, voltage controlled tunable phase shifters, FETs, and switches.

In another embodiment of the present invention, the probe 160 further comprises a plurality of parasitic elements, and a plurality of active tuning elements, as is shown in FIGS. 7 and 8. In this embodiment, the probe 160 includes a first parasitic element 210 and a first active tuning element 212 associated with the first parasitic element, wherein the first parasitic element and the first active element 212 are positioned to one side of the main probe element 170. The embodiment also includes a second parasitic element 232 and a second active tuning element 234 associated with the second parasitic element. The second parasitic element and the second active tuning element are positioned below the main probe element 170. In this case, the second parasitic and active tuning elements are used to tune the frequency characteristic of the probe 160, and in another embodiment, the first parasitic and active tuning elements are used to provide beam steering capability for the probe.

In one embodiment of the present invention, the radiation pattern associated with the probe is rotated in accordance with the first parasitic and active tuning elements. In some embodiments, this rotation may be ninety degrees.

Figure 9:
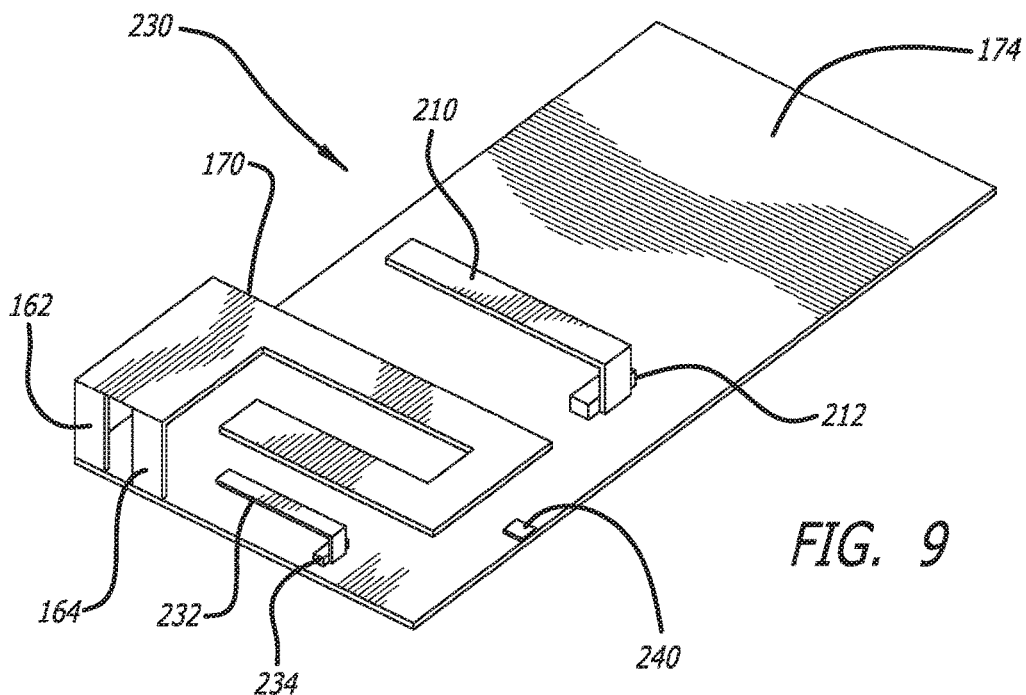
FIG. 9 is a perspective view of a hybrid IMD probe having two parasitic elements each with an active tuning element and a third active tuning element under the main conductive element of the probe, wherein the first and second parasitic elements and all three active tuning elements are usable to control the energy pattern, or beam, of the main IMD element in the internal storage area of the storage container.

In another embodiment of the present invention shown in FIG. 9, the probe 230 further includes a third active tuning element 240 associated with the main probe element 192. This third active tuning element is adapted to tune the frequency characteristics associated with the probe.

Figure 10:
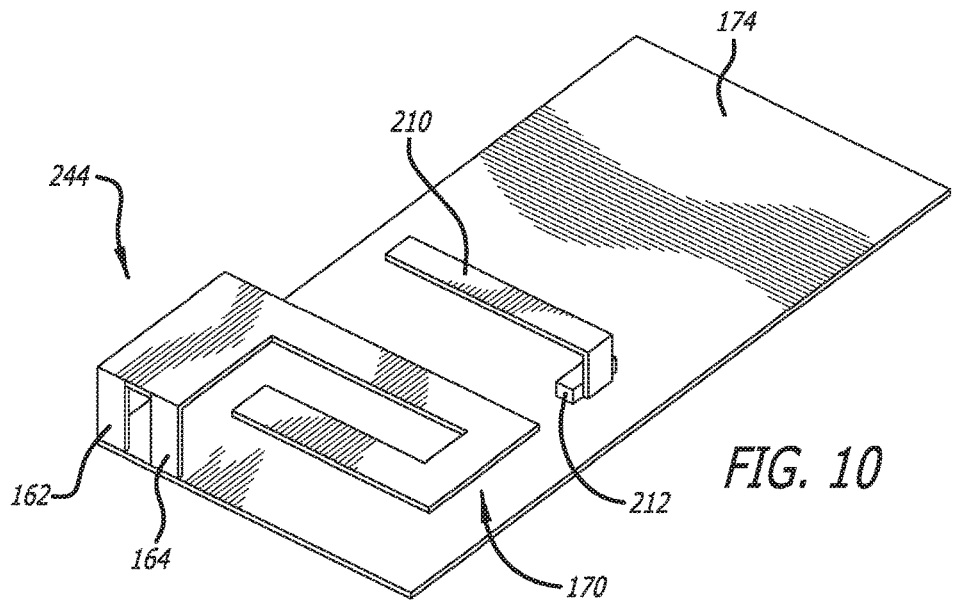
FIG. 10 is a perspective view of a hybrid IMD probe similar to that of FIGS. 7 and 8 but lacking a parasitic element under the main conducting slotted element of the probe.

Referring now to FIG. 10, a different embodiment of a hybrid IMD probe 244 is shown. In this embodiment, the hybrid IMD probe 244 includes a first parasitic element 210 and associated first active tuning element 212 but does not include the second parasitic element located under the main element 170 as shown in FIGS. 7, 8, and 9. The embodiment therefore has fewer parts, less programming in that a second active tuning element does not need to be controlled, nor is there a third active tuning element that needs to be controlled (see FIG. 9 for the first, second, and third active tuning elements 212, 232, and 240).

Figure 11:
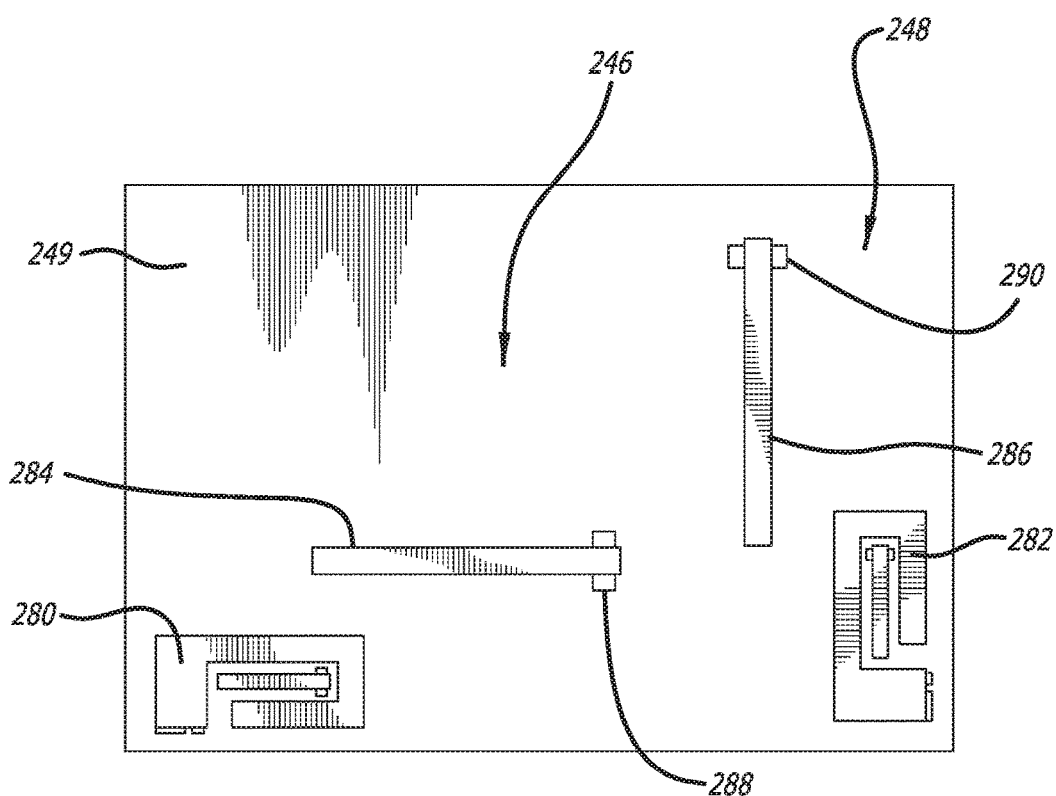
FIG. 11 is a top view of a dual hybrid IMD probe circuit board with two hybrid IMD probes located at ninety degrees from each other, to establish eight separate and selectable radiation patterns or beams for providing activating RF energy to a container to activate RFID tags locate on articles in the container.

Referring now to FIG. 11, a further embodiment is shown having dual hybrid IMD probes. In particular, two hybrid IMD probes 246 and 248 are located on the same circuit board 249. Each probe 246 and 248 includes a main conducting element 280 and 282 respectively, and a first parasitic element 284 and 286 with an active tuning element associated with both 288 and 290. It will be noted that these two co-located dual hybrid IMD probes are oriented so that they are ninety degrees from each other in this embodiment. The first parasitic element of each permits four separate radiation patterns or "beams" for each probe resulting in a total of eight radiation patterns 249 for the entire circuit board 249 of dual hybrid IMD probes. Because the two probes are oriented at a particular angle to each other, the eight radiation patterns do not overlap in this embodiment. However, in other embodiments, overlap may be desired and different orientations of the probes in relation to each other may be implemented. This embodiment is particularly applicable for use in larger containers, but may also be used in smaller containers as well.

Figure 12:
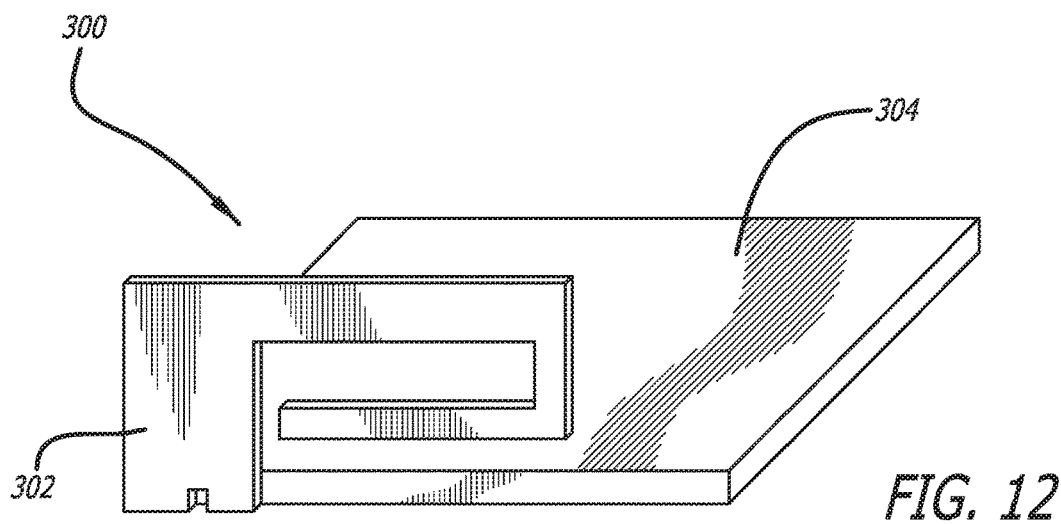
FIG. 12 is another embodiment of a hybrid IMD device having the same main conductive element as the IMD devices above, but being mounted orthogonally to the circuit board.

FIG. 12 presents a perspective view of a hybrid IMD probe 300 in which the main conducting element 302 is mounted orthogonally on the circuit board 304. Similar performance can be obtained with this configuration as described above.

Figure 13:
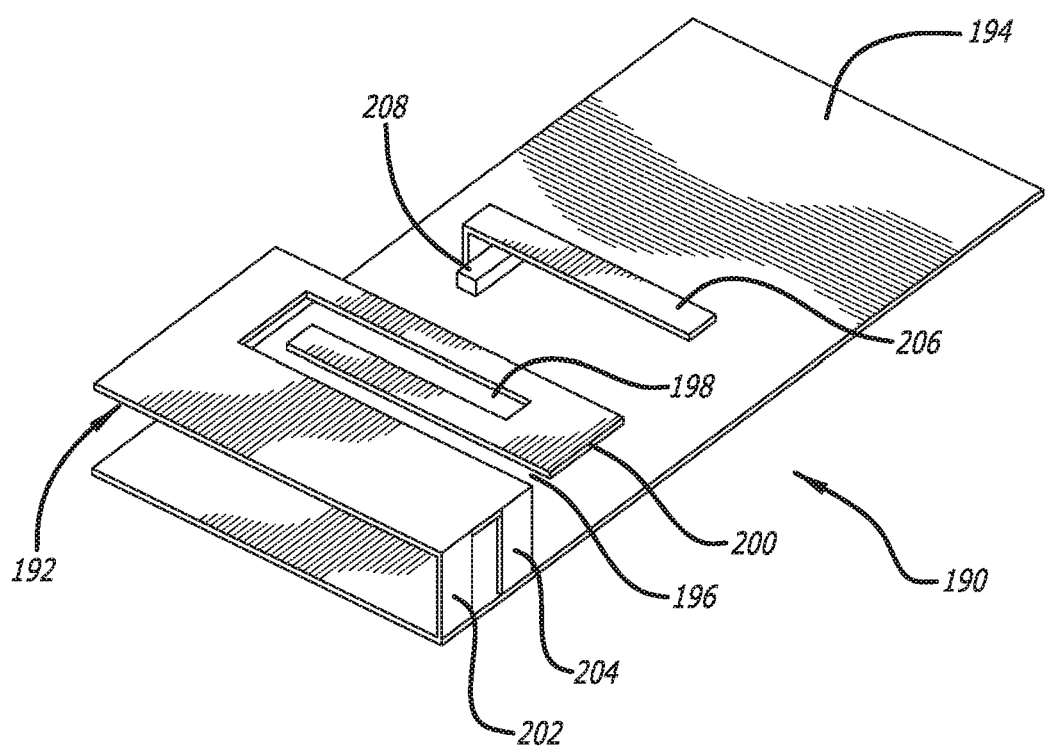
FIG. 13 is a perspective view of another embodiment of a hybrid IMD probe in which the main conducting element has two slots for capacitive coupling, and also showing a parasitic element with an associated active tuning element for providing selectable beams from the probe.

A second type of hybrid IMD probe 190 is shown in FIG. 13 and provides two resonances for use in dual frequency band or multi-band applications. This second type of hybrid IMD structure is composed of a planar main element 192 positioned above a ground plane 194. Two slots 196 and 198 are formed in one section of the planar conductor. The probe is excited in such a way that there are strong electric fields in the slot regions, with the slots being dimensioned to resonate at two different frequencies. The strong electric fields in the slot regions is a result of opposing currents flowing on two portions of a planar conductor that are parallel to one another. The two opposing currents on the conductor provide a magnetic field distribution similar to the fields formed by a half loop element above a ground plane, as is shown in FIG. 8. The result is a probe that has reduced fringing electric fields between the probe conductor and the ground plane, and a magnetic field distribution that is similar to a loop. A good mix of electric and magnetic fields are present in the near-field. The planar conductor 200 forming the probe is typically positioned above and in parallel to a ground plane 194. A conductor forming a feed leg 202 and a conductor forming a ground leg 204 are positioned orthogonal to the plane of the planar conductor. In this configuration the IMD probe forms a volume encompassed by the planar conductor and the ground plane, which determines the frequency bandwidth.

The parasitic element 206 and its associated active tuning element 208 result in multiple selectable radiation patterns or beams from the probe.

The planar slot configuration shown in the conductor shown in FIG. 13 provides equivalent radiated field performance as a pair of capacitive loops, one large loop and one small loop. The fields are equivalent due to the orientation of the slot configuration and the direction of current flow on individual portions or conductive sides of the slot.

Unlike other probes, such as the Planar Inverted F-Style Antenna (PIFA), the hybrid IMD probe 190 has an underlying advantage in that its properties depend mainly on the probe structure itself and not the surrounding area. In the hybrid IMD probe 190, the electrical currents are strongly localized to the probe region and do not propagate on the ground 194. This is an important feature as any probe employed for identifying RFID tags in metallized or shielded enclosures will by definition be in close proximity to large metal areas.

For further details on selecting or "steering" probe radiation patterns or beams, refer to U.S. Pat. No. 7,911,402, which is incorporated herein by reference.

Figure 14:
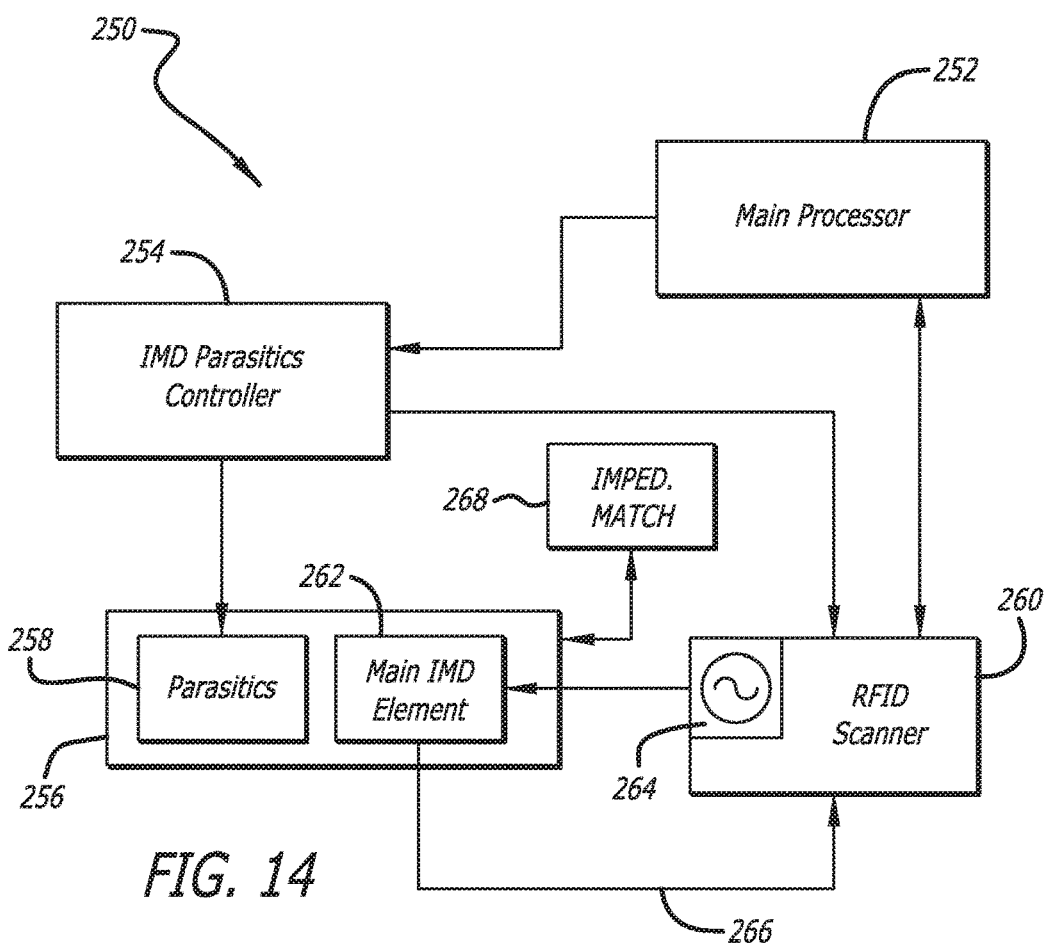
FIG. 14 is a block diagram of the control over a hybrid IMD probe including its parasitic elements in injecting RF activating energy into a cavity or container to activate RFID tags in the container.

Referring now to FIG. 14, In regard to the hybrid probes shown and described above having a parasitic element that provides for beam steering or radiation pattern selection, a main processor 252 signals the IMD parasitic controller 254 to select a particular beam of the probe 256 to activate. The parasitic controller then controls the various parasitic elements 258 and active tuning elements associated therewith to set the particular beam with which the probe will operate. The main processor 252 then controls the RFID reader 260 to provide activating RF energy to the main IMD element 262 through a signal generator 264. The probe 256 operates to inject activating RF energy to activate all RFID tags in the beam selected. The probe 256 is then controlled, in one embodiment, to receive the responsive signals from activated RFID tags in the container of interest, and forward the received responsive signals 266 to the RFID reader 260. Also shown is an active impedance matching control 268 to increase energy transfer between the probe 256 and a container.

In one case, the beam steering may be dynamic, in that the processor has the hybrid IMD probe change beams periodically. In another case, the beam selected for use by the probe is selected based on the location of the probe in the container, and that beam is fixed in that the probe only operates on that beam, or mode, for the entire life of the container. In one embodiment, the probe had four "beams" or "modes" at which the probe could be set.

Figure 15:
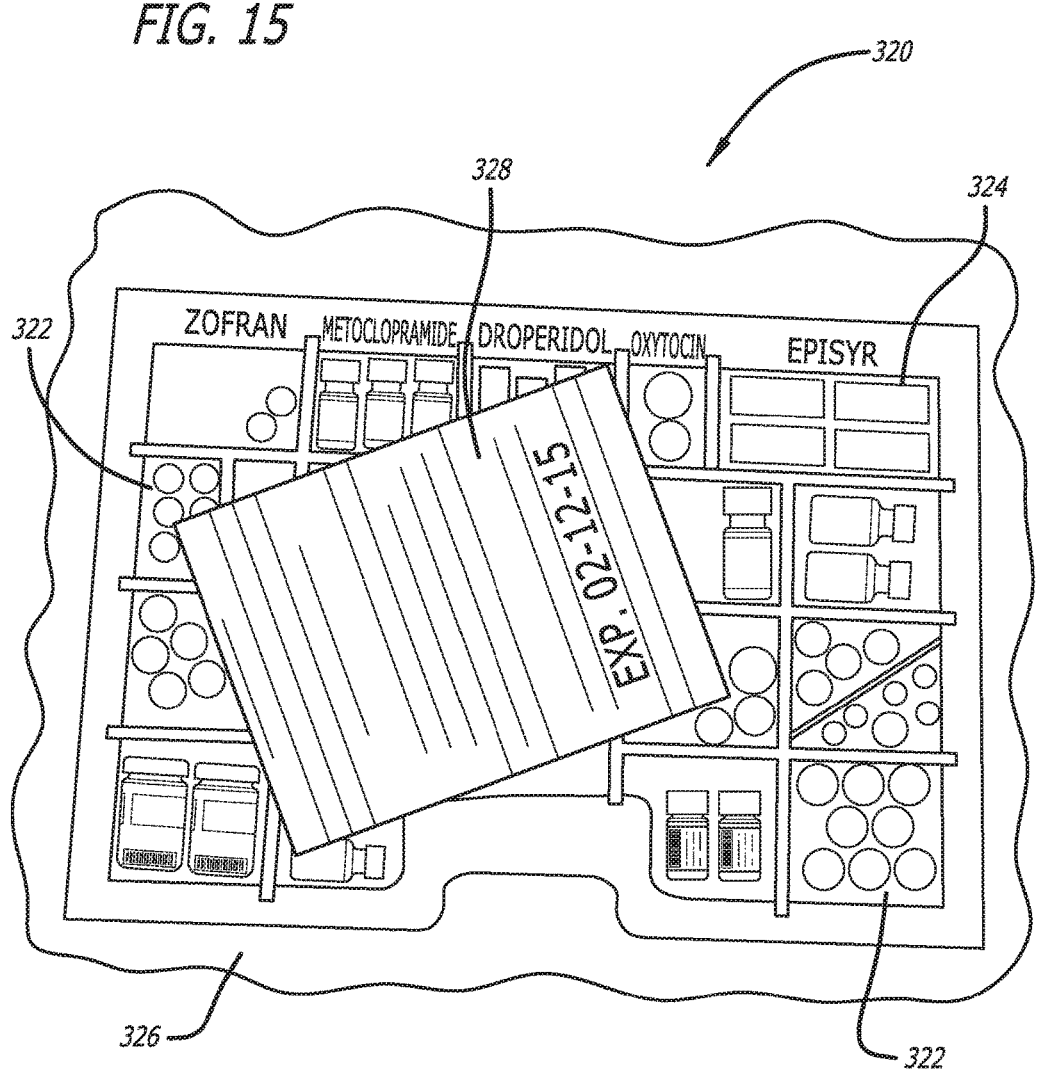
FIG. 15 is a perspective view of a code tray showing a single level of various medical articles, each of which has an attached RFID tag, and showing a paper with an expiration date printed thereon indicating the earliest date of expiration when one or more of the stored medical articles in the tray expires, the tray being sealed with transparent plastic material.

Referring now to FIG. 15, another type of container or storage system is commonly known as a tray or code tray, and may have other names. The code is typically used to identify the medical purpose of the tray, such as a "code blue" tray to resuscitate a person undergoing cardiac arrest. Such a tray may be formed of non-metallic material such as composites or plastics. The tray holds all of the medications, tools, and equipment that are expected to be required to complete a medical procedure or to handle a particular medical event.

A tray is typically laid out and displayed in an easily recognizable fashion. Color may be used also to assist in managing the inventory of the tray. This allows an assistant to retrieve the correct medication or instrument without delay. In the event that a surgeon is looking for the optimum tool or medication, a quick glance at the surgical tray will allow the identification of all available tools at his or her disposal. Labels are often placed on the tray also that specify what is in the pockets of the tray.

An example of such a medical "tray" is shown in FIG. 15. The tray 320 is a single layer and includes various pharmaceuticals 322 and other medical articles, such as pre-loaded syringes 324 (epinephrine syringe, lidocaine syringe, and an atropine syringe). The entire tray is sealed with clear plastic wrap 326 and an inventory list 328 is contained just under the plastic seal so that it is visible and readable without breaking the seal. The Required Inventory list in this case identifies the name of the tray, such as "Childbirth Tray," lists the contents of the tray, and includes other information such as the first expiration date of any of the articles contained in the tray. The Required Inventory list may also contain a plan layout of the tray showing which articles should be stored where. It may have multiple pages or only a single page.

The tray 320 has been prepared by a pharmacist at the pharmacy because it has prescription medications in it (oxycontin for example). The Required Inventory list may also include brand names as well as generic names, and National Drug Codes ("NDCs") or Universal Product Codes ("UPCs") as part of the inventory. State regulations typically allow a hospital or other facility to define the contents of its trays, and therefore they can be selected based on particular "community" standards and requirements. State regulations, typically require that the hospital have specific procedures to ensure accuracy of tray contents. Such procedures include inventory and restocking procedures, as well as detection of expired and recalled medical articles. In the example of FIG. 14, the tray is relatively small. However for other purposes, a tray can be much larger with many more medical articles. Some trays may include additional layers that may or may not include additional items not contained in the top layer.

If the seal is broken, regardless of whether any of the contents were removed, an inventory will likely be required. Existing processes require that this be done manually. Each of the articles in the tray is examined to determine if it is expired or recalled, and is compared against the Required Inventory list to determine if it should be in the tray. The Required Inventory list is also referenced for checking that all required articles are in the tray and that extra articles are not in the tray. Once it has been restocked, the tray 320 is resealed 326 and may be placed on the floor again for medical use. Such examination and restocking can take significant amounts of time and if a pharmacist is required to perform some of the inventory process, that pharmacist will be unavailable to perform other duties. In such a manual procedure, mistakes can be made. Thus, a need has been identified to provide a more efficient and accurate system and method to restock such carts and trays.

Crash carts and trays must be resupplied periodically to replace expired or recalled items, and if a cart or a tray was actually used, to replace consumed articles. As mentioned, such processes are typically performed manually at a significant cost in time. Missing key medical articles in a tray could be devastating in an emergency situation. Therefore accuracy in the resupply is mandatory. Often, trays that have articles that are just nearing expiration must be returned to the pharmacy for resupply in advance of expiration due to the time it takes to process the tray. Any recalled articles must also be removed and substitutions made. It is also possible that items foreign to the crash cart or tray have been added while they were in the field, and these foreign articles must be found and removed.

Unfortunately, the above procedures tend to suffer from significant shortcomings. For instance, manual inspections can result in errors as can resupply. Creating records of what was done is also generally time consuming and error prone, all of which drive up the cost of creating and resupplying the carts and trays. There has therefore been recognized a need for improvement in managing such crash carts and trays.

Furthermore, under the current system, the pharmacy is unable to create individualized carts for patients. For example, certain patients may be provided a patient-specific cocktail of drugs (this may be a mixed vial or a combination of drugs). Because these are non-standard drugs or drug combinations, a pharmacist has to double check a drug list or a prescription list when creating a cocktail drug or filling a personalized cart with medical items.

Figure 16:
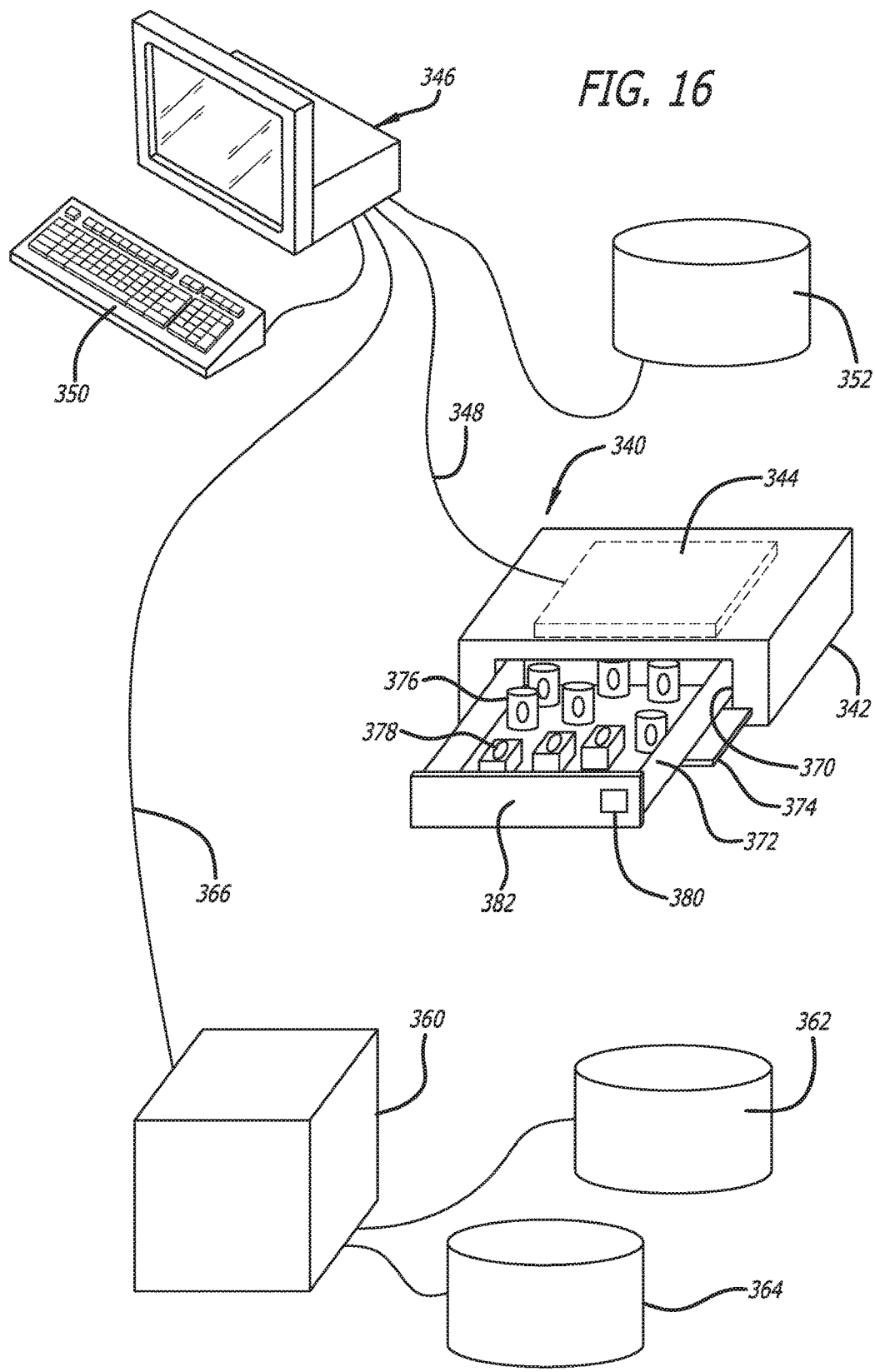
FIG. 16 is a system for reading the RFID tags of the medical articles in the tray of the FIG. 15 comprising a box which provides electromagnetic shielding around the tray, and an RFID reader as well as a hybrid IMD probe for activating and reading RFID tags that are within the tray.

FIG. 16 shows an embodiment of an inventory management system 340 according to aspects of the invention. An enclosure 342 is shown, which in this case creates an EM energy shielded cage in that all the walls and top and bottom are electrically shielded to isolate the enclosure by preventing (or significantly attenuating) EM from entering or escaping the enclosure. The enclosure is fitted with a reader 344 configured to interrogate RFID tags located within the enclosure. One or more hybrid IMD probes are locate within the enclosure 342 and are connected to the reader 344.

The reader 344 is connected to a computer 346 through a connection 348. The connection 348 may be a wired connection, wireless connection, or any other suitable connection for data transfer. In one embodiment, the physical body of the computing system may be attached to the enclosure 342. The computing system 346 has a non-volatile memory 354 in which is stored at least one database ("db") which may be a local database, or other. The non-volatile memory 354 comprises one or more computer readable media within the computer system 346 and may be located within the computer itself or external to the computer. The memory is shown here as being outside the computer only for clarity of illustration in the discussion and is not meant to limit the invention in any way. In another embodiment, part or all of the local database may be held on a server 360. The computing system 346 is also connected to the remote database 360 at which is located a first remote database 362 and a second remote database 364. As in the local computer, these remote databases may be stored on a memory that is internal to the server or that is external to the server. Further, the server 360 may be located nearby the local computer 346 or may be remote therefrom. By remote, it is meant that it may be in the same room, or in the same wing, or in the same facility, or may be in the cloud. Connection 366 to the server 360 may likewise be a wired connection, wireless connection, or any other suitable connection for data transfer.

In one embodiment, the data held on the local database 352 may depend on the location/specialty/facility using computer system 346. For example, if the computer system 346 were stationed in an emergency room ("ER"), the local database 352 may hold only information or data regarding medical articles, medical containers, and other inventory most used in an ER. In one embodiment, the remote database 362 at the server 360 may serve as a main database and contain data for all medical articles, medical containers, and other inventory for all medical locations/facilities/specialties. The local database 352 may maintain a copy of the portion of data held on the remote database 362 that is most relevant to the computer system 346, but can access the remote database 362 when encountering medical items, medical containers, or other inventory for different facilities/specialties/locations.

The enclosure 342 has an opening 370 through which a tray 372 may be slid into the enclosure. The tray is placed completely within the enclosure so that the front door 374 can be closed over the opening 370 to complete the Faraday cage of the enclosure 342. The tray includes a number of medical items 376 with each one having an RFID tag 378 attached. As discussed previously, each RFID tag has a stored different identification number comprising a few bytes with a check digit. The error codes are not stored in the tag memory. They are generated on the fly. Manufacturers guarantee that each serial number is used only once. Some RFID tags have more complex codes for identifying the RFID tag. In this case, the tray 372 also has an RFID tag 280 attached to its outer surface 382. The reader 344 will read those identification numbers from the tags, communicate them to the computer which will compare them against one or more databases either locally 352 or remotely through a server 362 and/or 364. The process of using the identification numbers of the tags is discussed below.

Medical item information may include information such as name, lot code, date of manufacture, expiration date, dosage, weight, color, and an image of the medical article. In one embodiment, the identification ("ID") data may be partially made of drug codes that identify the drugs. As an example and not by way of limitation, the identification data may use the National Drug Code ("NDC") as part of its data allowing for easy identification of the attached medical item. Identification data may also have other identifying codes that establish the manufacturer, lot code, dosage, drug type, expiration date, etc.

Shown in FIG. 16 is an enclosure 342 formed in accordance with aspects of the invention by which it is much smaller than an enclosure sized to be resonant at the operating frequency of RFID yet the EM field within the enclosure 342 is highly robust and effective at exciting and reading all RFID tags located therein due to the use of a hybrid IMD probe or probes. Because inventive aspects are incorporated, the enclosure is much smaller than other enclosures and is therefore highly desirable in areas where space is limited, such as a pharmacy in a healthcare facility. Although not shown, the front door 374 includes latching hardware to retain it in a closed when it is rotated upwards and put in use. A handle 384 assists in managing the configuration of the front door. The enclosure is formed of a metallic mesh or other EM shielding material to provide an EM shielded cage about trays that are slid within it for scanning and inventorying. The front door in this embodiment is also formed of an RF shielding material. An RFID reader 344 is shown in dashed lines which may also contain a hybrid IMD probe or probes, the electronics, and a battery 388 for the enclosure. The electronics include a processor, communications, wired and wireless connections, and a local power source. In another embodiment, an AC adapter may be included for using wall power. Communications ability over networks is provided.

The approximate volume for a resonant enclosure at an RFID operating frequency of 900 MHz is 3 ft.×3 ft.×3 ft. for a total of 27 cubic feet. In one embodiment, the enclosure 342 had the dimensions of 2.25 ft. wide by 1.6 ft. long by 0.88 ft. high for an approximate volume of 3.15 cubic feet, and with the use of a hybrid IMD probe or probes, achieved equally effective electric and magnetic fields within the enclosure at exciting and reading all RFID tags located therein. The difference in sizes of the two enclosures makes one formed in accordance with the invention more attractive in many situations where space is limited.

The above may also be combined with a frequency hopping arrangement and a Return Signal Sensitivity Indicator arrangement for increasing the likelihood of activating all RFID tags in a particular container. For further details on such arrangements, see U.S. Patent Application Publication No. 2014/0184391, application Ser. No. 14/142,749, now U.S. Pat. No. 9,349,030 which is incorporated herein by reference.

The invention is intended to provide a read process that ensures the highest statistical probability of identifying all RFID tags contained in the RF-enabled enclosure.

Although shown and described in the embodiment of a medical article tracking system and method, the invention can have application to other fields of tracking outside the medical field.

A Faraday cage is mentioned; however, this device is also known as a Faraday shield and Faraday screen. In addition, other EM shielding is usable. Different EM shielding can produce the desired isolation of keeping activating RF energy within the container so that RFID tags located outside the container are not activated and read. Mistakenly reading RFID tags that are located outside the container can cause errors since the tracking system of the container will not be able to determine that the RFID tag is outside the container and will return a result showing that it is in the container.

Although RFID tags are used herein as an embodiment, other data carriers that communicate through electromagnetic energy may also be usable.

Unless the context requires otherwise, throughout the specification and claims that follow, the word "comprise" and variations thereof, such as, "comprises" and "comprising" are to be construed in an open, inclusive sense, which is as "including, but not limited to."

Although RFID tags are used herein as an embodiment, other data carriers that communicate through electromagnetic energy may also be usable.

Unless the context requires otherwise, throughout the specification and claims that follow, the word "comprise" and variations thereof, such as, "comprises" and "comprising" are to be construed in an open, inclusive sense, which is as "including, but not limited to."

While the invention has been described in connection with what is presently considered to be the most practical and preferred embodiments, it is to be understood that the invention is not to be limited to the disclosed embodiments and elements, but, to the contrary, is intended to cover various modifications, combinations of features, equivalent arrangements, and equivalent elements included within the spirit and scope of the appended claims.

I claim:

1. A tracking system for medical articles stored in an interior volume of a container, each of the medical articles having wireless identification device that is configured to respond with its respective identification data upon receiving activation energy, the interior volume of the container having a resonant frequency that is different from a frequency of operation of the wireless identification device, the system comprising:

electromagnetic ("EM") shielding located about the interior volume of the container to shield the interior volume of the container from the passage of EM energy both into and out of the interior volume, whereby the interior volume is isolated to keep activating radio frequency ("RF") energy within the container so that wireless identification devices located outside the container are not activated and read;

an EM energy conducting injection probe located within the EM shielding, the injection probe located and configured to inject activation RF energy into the interior volume having an energy pattern directed to fill the interior volume of the container with an EM field, wherein the injection probe comprises a main conductive element having capacitive coupling thereby forming an isolated electric field that fills the interior volume of the container, and wherein the main conductive element is spaced apart from a ground plane by a selected distance thereby forming a robust magnetic field that is orthogonal to the electric field and that also fills the interior volume of the container;

a parasitic element located at a selected position in relation to the main conductive element of the probe, the parasitic element being configured to control the energy pattern of the main conductive element in the internal volume of the container;

a signal source producing activation RF energy having a frequency that is different from the resonant frequency of the interior volume of the container, and coupled to the probe; and a processor connected with the signal source, the processor being programmed to control the signal source to deliver the activation RF energy to the injection probe for injecting into the interior volume of the container to activate identification devices in the interior volume, the processor further being programmed to stop the signal source from delivering RF energy to the injection probe to allow identification signals from activated identification devices in the interior volume to be received.

2. The medical article tracking system of claim 1 wherein the injection probe comprises a hybrid isolated magnetic dipole device in which the electric field and the magnetic field are circularly polarized.

3. The medical article tracking system of claim 1 wherein the injection probe includes a controllable active tuning element connected with the parasitic element to alter the effect of the parasitic element on the main conductive element to controllably change the energy pattern.

4. The medical article tracking system of claim 3 further comprising:

a controllable active tuning element connected with the parasitic element to alter the effect of the parasitic element on the main conductive element to controllably change the energy pattern of the main conductive element in the internal volume of the container;

wherein the processor is connected with the controllable active tuning element of the parasitic element and the processor being further programmed to control the active tuning element of the parasitic element to beam steer the EM energy pattern in the interior volume.

5. The medical article tracking system of claim 1 further comprising a dual injection probe circuit in which a plurality of injection probes are co-located and positioned in relation to each other to provide multiple energy patterns into the interior volume.

6. The medical article tracking system of claim 5 wherein the dual injection probe circuit comprises a first injection probe disposed at a first angle that provides a first beam and a second injection probe disposed at a second angle that provides a second beam of energy wherein the second angle is selected in relation to the first angle so that the first and second beams overlap in the interior volume.

7. The medical article tracking system of claim 5 wherein the dual injection probe circuit comprises a first injection probe disposed at a first angle that provides a first beam and a second injection probe disposed at a second angle that provides a second beam of energy wherein the second angle is selected in relation to the first angle so that the first and second beams do not overlap in the interior volume.

8. The medical article tracking system of claim 1 further comprising an active tuned impedance matching circuit connected with the injection probe that controls impedance of the injection probe to more closely match the impedance of the interior volume of the container whereby increased efficiency in electromagnetic energy transfer into the interior volume of the container results.

9. The medical article tracking system of claim 1 wherein the processor is also connected with the injection probe and wherein upon stopping the signal source from delivering RF energy to the injection probe, the processor receives identification signals from activated identification devices in the interior volume through the probe.

10. The medical article tracking system of claim 1 further including a receiving antenna located within the EM shielding, the processor being connected with the receiving antenna and programmed to receive the identification signals from activated identification devices in the interior.

11. The medical article tracking system of claim 1 wherein the parasitic element is located between the conducting element and ground.

12. The medical article tracking system of claim 1 wherein the main conductive element comprises a conductive element disposed above a ground plane with the main conductive element having two slots, the slots being dimensioned to resonate at two different frequencies.

13. A method for tracking medical articles stored in the interior volume of a container, the interior volume of the container having a size selected to receive a plurality of medical articles each of which has a wireless identification device associated therewith that has individual identification data, and each wireless identification device configured to respond with identification data upon receiving activation energy, the interior volume of the container having a resonant frequency that is different from a frequency of operation of the wireless identification device, the method comprising:
shielding the interior volume of the container from the passage of electromagnetic ("EM") energy from the passage of electromagnetic energy both into and out of the interior volume, whereby the interior volume is isolated to keep activating RF energy within the container so that RFID tags located outside the container are not activated and read;
injecting activating radio frequency ("RF") energy into the interior volume in an energy pattern with an injection probe located within the EM shielding to fill the interior volume with an EM field, wherein the injection probe comprises a main conductive element having capacitive coupling across at least one slot of the main conductive element thereby forming an isolated electric field that fills the interior of the container, and wherein the main conductive element is spaced apart from a ground plane by a selected distance thereby forming a robust magnetic field that is orthogonal to the electric field and that also fills the interior of the container;
controlling the energy pattern in the interior volume with a parasitic element located at a selected position in relation to the main conductive element of the injection probe;
delivering activating RF energy to the injection probe from a signal source, the activating energy having a frequency that is different from the resonant frequency of the interior volume of the container;
controlling the signal source to deliver the activating energy to the injection probe for injection into the interior volume, and controlling the signal source to stop delivering activating energy to the injection probe, whereby responsive identification signals from activated identification devices located in the interior volume can be received.

14. The method of claim 13 wherein the step of injecting activating RF energy into the interior volume in an energy pattern with an injection probe comprises using an injection probe that comprises a hybrid isolated magnetic dipole device in which the electric and magnetic fields are circularly polarized.

15. The method of claim 13 wherein the step of injecting activating RF energy into the interior volume in an energy pattern with an injection probe comprises using an injection probe that comprises a controllable active tuning element connected with the parasitic element to alter the effect of the parasitic element on the main conductive element to controllably change the energy pattern.

16. The method for tracking medical articles of claim 15 wherein the step of controlling the signal source further comprises receiving the identification signals from activated identification devices located in the interior volume with a receiving antenna located within the EM shielding which is separate from the probe.

17. The method for tracking medical articles of claim 15 wherein the step of controlling the energy pattern in the interior volume with a parasitic element further comprises controlling the tuning of the parasitic element to alter the effect of the parasitic element on the main conductive element to beam steer the EM energy pattern in the interior volume.

18. The method of claim 13 wherein the step of injecting activating RF energy into the interior volume in an energy pattern with an injection probe comprises using an injection probe that comprises a dual probe circuit in which a plurality of probes are co-located and positioned in relation to each other to provide multiple radiation patterns into the interior volume.

19. The method for tracking medical articles of claim 18 wherein the step of injecting activation RF energy into the interior volume comprises injecting energy into the interior volume at a first angle in a first beam by a first injection probe and injecting energy into the interior volume at a second angle in a second beam by a second injection probe wherein the first and second angles are selected so that the first and second beams overlap in the interior volume.

20. The method for tracking medical articles of claim 18 wherein the step of injecting activation RF energy into the interior volume comprises injecting energy into the interior volume at a first angle in a first beam by a first injection probe and injecting energy into the interior volume at a second angle in a second beam by a second injection probe wherein the first and second angles are selected so that the first and second beams do not overlap in the interior volume.

21. The method of claim 13 wherein the step of injecting activating RF energy into the interior volume in an energy pattern with an injection probe comprises using an injection probe having an active tuned impedance matching circuit that is configured to control impedance of the injection probe to more closely match the impedance of the interior volume of the container whereby increased efficiency in electromagnetic energy transfer into the interior volume of the container results.

22. The method for tracking medical articles of claim 13 wherein the step of stopping the signal source from delivering RF energy to the injection probe further comprises the step of receiving the identification signals from activated identification devices located in the interior volume through the injection probe.

23. The method for tracking medical articles of claim 13 wherein the step of controlling the energy pattern in the interior volume with a parasitic element comprises controlling the energy pattern with a parasitic element that is located between the conducting element and ground.

24. The method for tracking medical articles of claim 13 wherein the step of injecting activating RF energy into the interior volume comprises forming an electric field and a magnetic field with a main conductive element disposed above a ground plane with the main conductive element having two slots, the slots being dimensioned to resonate at two different frequencies.

25. A tracking system for medical articles stored in an interior volume of a container, each of the medical articles having a wireless identification device that is configured to respond with its respective identification data upon receiving activation energy, the interior volume of the container having a resonant frequency that is different from a frequency of operation of the wireless identification device, the system comprising:

electromagnetic ("EM") shielding located about the interior volume of the container to shield the interior volume of the container from the passage of EM energy both into and out of the interior volume, whereby the interior volume is isolated to keep activating radio frequency ("RF") energy within the container so that wireless identification devices located outside the container are not activated and read;

an EM energy conducting injection probe located within the EM shielding, the injection probe located and configured to inject activation RF energy into the interior volume, the activation energy having an EM energy pattern, wherein the injection probe comprises a hybrid isolated magnetic dipole device in which the electric field and the magnetic field are circularly polarized, the dipole device comprising a main conductive element having capacitive coupling thereby forming an isolated electric field in the interior volume of the container, and wherein the main conductive element is spaced apart from a ground plane by a selected distance thereby forming a robust magnetic field that is orthogonal to the electric field and that also is directed to the interior volume of the container;

a parasitic element located at a selected position in relation to the main conductive element of the probe, the parasitic element comprising a controllable active tuning element connected with the parasitic element to alter the effect of the parasitic element on the main conductive element to controllably change the energy pattern of the main conductive element in the internal volume of the container;

a signal source producing activation RF energy having a frequency that is different from the resonant frequency of the interior volume of the container, and coupled to the probe; and a processor connected with the signal source and the controllable active tuning element of the parasitic element, and being programmed to control the signal source to deliver the activation RF energy to the injection probe for injecting into the interior volume of the container to activate identification devices in the interior volume, the processor further being programmed to control the active tuning element of the parasitic element to beam steer the EM energy pattern in the interior volume.

26. A method for tracking medical articles stored in the interior volume of a container, the interior volume of the container having a size selected to receive a plurality of medical articles each of which has a wireless identification device associated therewith that has individual identification data, and each wireless identification device configured to respond with identification data upon receiving activation energy, the interior volume of the container having a resonant frequency that is different from a frequency of operation of the wireless identification device, the method comprising:

shielding the interior volume of the container from the passage of electromagnetic ("EM") energy from the passage of electromagnetic energy both into and out of the interior volume, whereby the interior volume is isolated to keep activating RF energy within the container so that RFID tags located outside the container are not activated and read;

injecting activating radio frequency ("RF") energy into the interior volume in an energy pattern with an injection probe located within the EM shielding, the injection probe comprising a hybrid isolated magnetic dipole device in which the electric and magnetic fields are circularly polarized, wherein the injection probe that comprises a main conductive element having capacitive coupling across at least one slot of the main conductive element thereby forming an isolated electric field that fills the interior of the container, and wherein the main conductive element is spaced apart from a ground plane by a selected distance thereby forming a robust magnetic field that is orthogonal to the electric field and that also fills the interior of the container;

controlling the energy pattern in the interior volume with a parasitic element located at a selected position in relation to the main conductive element of the injection probe, wherein the parasitic element comprises a controllable active tuning element configured to alter the effect of the parasitic element on the main conductive element to thereby controllably change the energy pattern;

delivering activating RF energy to the probe from a signal source, the activating energy having a frequency that is different from the resonant frequency of the interior volume of the container;

receiving within the EM shielding identification data response signals from activated wireless identification devices located within the interior volume, the receiving antenna providing the received identification data response signals; and controlling the signal source to deliver the activating energy to the injection probe for injection into the interior volume to activate identification devices in the interior volume and controlling the controllable active tuning element of the parasitic element to beam steer the EM energy pattern in the interior volume.

* * * * *